United States Patent
McClintock et al.

(10) Patent No.: US 12,114,898 B2
(45) Date of Patent: Oct. 15, 2024

(54) MODULAR HEAD ASSEMBLY FOR SPINAL FIXATION

(71) Applicant: K2M, Inc., Leesburg, VA (US)

(72) Inventors: Larry E. McClintock, Gore, VA (US); Michael Barrus, Redondo Beach, CA (US)

(73) Assignee: K2M, Inc., Leesburg, VA (US)

( * ) Notice: Subject to any disclaimer, the term of this patent is extended or adjusted under 35 U.S.C. 154(b) by 0 days.

(21) Appl. No.: 17/560,471

(22) Filed: Dec. 23, 2021

(65) Prior Publication Data

US 2023/0270472 A1    Aug. 31, 2023

Related U.S. Application Data

(63) Continuation-in-part of application No. PCT/US2021/059376, filed on Nov. 15, 2021.

(60) Provisional application No. 63/115,737, filed on Nov. 19, 2020.

(51) Int. Cl.
*A61B 17/70* (2006.01)

(52) U.S. Cl.
CPC ...... *A61B 17/7038* (2013.01); *A61B 17/7037* (2013.01)

(58) Field of Classification Search
CPC .............. A61B 17/7032; A61B 17/7035–7038
See application file for complete search history.

(56) References Cited

U.S. PATENT DOCUMENTS

| | | | |
|---|---|---|---|
| 856,265 A | 6/1907 | Kunkle | |
| 5,382,248 A | 1/1995 | Jacobson et al. | |
| 5,487,744 A | 1/1996 | Howland | |
| 5,549,608 A | 8/1996 | Errico et al. | |
| 5,554,157 A | 9/1996 | Errico et al. | |
| 5,575,972 A | 11/1996 | Mitsuhashi et al. | |
| 5,578,033 A | 11/1996 | Errico et al. | |
| 5,584,834 A | 12/1996 | Errico et al. | |
| 5,586,984 A | 12/1996 | Errico et al. | |
| 5,609,593 A | 3/1997 | Errico et al. | |

(Continued)

FOREIGN PATENT DOCUMENTS

| | | |
|---|---|---|
| EP | 2873383 A1 | 5/2015 |
| WO | 2020056385 A1 | 3/2020 |

OTHER PUBLICATIONS

International Search Report issued in Appln. No. PCT/US2021/059376 mailed Feb. 3, 2022 (2 pages).

(Continued)

*Primary Examiner* — Eduardo C Robert
*Assistant Examiner* — Michelle C Eckman
(74) *Attorney, Agent, or Firm* — Lerner David LLP

(57) ABSTRACT

A modular pedicle screw for spinal fixation. The pedicle screw includes a bone screw and a modular head assembly. The bone screw having a head and a shank, the head defining at least one groove. The modular head assembly includes a housing having a proximal end, a distal end and a throughbore extending along a longitudinal axis of the housing between the proximal and distal ends of the housing, and an anvil disposed within the throughbore. The modular head assembly includes at least one protrusion sized and shaped to be received by the at least one groove for restricting relative movement between the housing and the bone screw to a single plane.

20 Claims, 15 Drawing Sheets

(56) References Cited

U.S. PATENT DOCUMENTS

| | | |
|---|---|---|
| 5,609,594 A | 3/1997 | Errico et al. |
| 5,669,911 A | 9/1997 | Errico et al. |
| 5,725,528 A | 3/1998 | Errico et al. |
| 5,733,285 A | 3/1998 | Errico et al. |
| 5,735,851 A | 4/1998 | Errico et al. |
| 5,800,435 A | 9/1998 | Errico et al. |
| 5,817,094 A | 10/1998 | Errico et al. |
| 6,004,322 A | 12/1999 | Bernstein |
| 6,050,997 A | 4/2000 | Mullane |
| 6,146,383 A | 11/2000 | Studer et al. |
| 6,280,442 B1 | 8/2001 | Barker et al. |
| 6,482,207 B1 | 11/2002 | Errico |
| 6,623,485 B2 | 9/2003 | Doubler et al. |
| 6,660,004 B2 | 12/2003 | Barker et al. |
| 6,669,697 B1 | 12/2003 | Pisharodi |
| 6,733,502 B2 | 5/2004 | Altarac et al. |
| 6,837,889 B2 | 1/2005 | Shluzas |
| 6,869,433 B2 | 3/2005 | Glascott |
| 6,887,242 B2 | 5/2005 | Doubler et al. |
| 7,066,937 B2 | 6/2006 | Shluzas |
| 7,087,057 B2 | 8/2006 | Konieczynski et al. |
| 7,144,396 B2 | 12/2006 | Shluzas |
| 7,186,255 B2 | 3/2007 | Baynham et al. |
| 7,306,606 B2 | 12/2007 | Sasing |
| 7,314,467 B2 | 1/2008 | Howland |
| 7,322,981 B2 | 1/2008 | Jackson |
| 7,662,175 B2 | 2/2010 | Jackson |
| 7,682,377 B2 | 3/2010 | Konieczynski et al. |
| 7,722,645 B2 | 5/2010 | Bryan |
| 7,727,261 B2 | 6/2010 | Barker et al. |
| 7,749,258 B2 | 7/2010 | Biedermann et al. |
| 7,766,943 B1 | 8/2010 | Fallin et al. |
| 7,766,945 B2 | 8/2010 | Nilsson et al. |
| 7,776,067 B2 | 8/2010 | Jackson |
| 7,785,354 B2 | 8/2010 | Biedermann et al. |
| 7,789,896 B2 | 9/2010 | Jackson |
| 7,833,250 B2 | 11/2010 | Jackson |
| 7,842,073 B2 | 11/2010 | Richelsoph et al. |
| 7,879,075 B2 | 2/2011 | Shluzas |
| 7,901,435 B2 | 3/2011 | Slivka et al. |
| 7,942,909 B2 | 5/2011 | Hammill, Sr. et al. |
| 7,942,910 B2 | 5/2011 | Doubler et al. |
| 7,942,911 B2 | 5/2011 | Doubler et al. |
| 7,947,065 B2 | 5/2011 | Hammill, Sr. et al. |
| 7,951,172 B2 | 5/2011 | Chao et al. |
| 7,951,173 B2 | 5/2011 | Hammill, Sr. et al. |
| 8,007,518 B2 | 8/2011 | Winslow et al. |
| 8,012,181 B2 | 9/2011 | Winslow et al. |
| 8,016,861 B2 | 9/2011 | Mitchell et al. |
| 8,048,115 B2 | 11/2011 | Winslow et al. |
| 8,048,126 B2 | 11/2011 | Altarac et al. |
| 8,048,133 B2 | 11/2011 | Biedermann et al. |
| 8,052,724 B2 | 11/2011 | Jackson |
| 8,057,515 B2 | 11/2011 | Flynn et al. |
| 8,057,519 B2 | 11/2011 | Justis et al. |
| 8,066,744 B2 | 11/2011 | Justis et al. |
| 8,075,603 B2 | 12/2011 | Hammill, Sr. et al. |
| 8,083,772 B2 | 12/2011 | Winslow et al. |
| 8,083,775 B2 | 12/2011 | Winslow et al. |
| 8,083,777 B2 | 12/2011 | Butters et al. |
| 8,088,152 B2 | 1/2012 | Schumacher |
| 8,092,501 B2 | 1/2012 | Mitchell et al. |
| 8,092,504 B2 | 1/2012 | Warnick |
| 8,097,024 B2 | 1/2012 | Winslow et al. |
| 8,097,025 B2 | 1/2012 | Hawkes et al. |
| 8,100,946 B2 | 1/2012 | Strausbaugh et al. |
| 8,114,134 B2 | 2/2012 | Winslow et al. |
| 8,133,262 B2 | 3/2012 | Whipple |
| 8,137,384 B2 | 3/2012 | Heiges et al. |
| 8,137,386 B2 | 3/2012 | Jackson |
| 8,142,481 B2 | 3/2012 | Warnick |
| 8,147,522 B2 | 4/2012 | Warnick |
| 8,167,912 B2 | 5/2012 | Jacofsky et al. |
| 8,172,876 B2 | 5/2012 | Janowski et al. |
| 8,192,468 B2 | 6/2012 | Biedermann et al. |
| 8,192,470 B2 | 6/2012 | Biedermann et al. |
| 8,197,518 B2 | 6/2012 | Hammill, Sr. et al. |
| 8,211,155 B2 | 7/2012 | Winslow et al. |
| 8,216,281 B2 | 7/2012 | Winslow et al. |
| 8,221,471 B2 | 7/2012 | Kovach et al. |
| 8,257,397 B2 | 9/2012 | Winslow et al. |
| 8,267,969 B2 | 9/2012 | Altarac et al. |
| 8,298,265 B2 | 10/2012 | Purcell et al. |
| 8,298,274 B2 | 10/2012 | Barker, Jr. et al. |
| 8,333,792 B2 | 12/2012 | Winslow et al. |
| 8,337,530 B2 | 12/2012 | Hestad et al. |
| 8,337,536 B2 | 12/2012 | Mitchell et al. |
| 8,372,122 B2 | 2/2013 | Winslow et al. |
| 8,394,127 B2 | 3/2013 | Winslow et al. |
| 8,398,689 B2 | 3/2013 | Abdou |
| 8,430,916 B1 | 4/2013 | Winslow et al. |
| 8,444,681 B2 | 5/2013 | Jackson et al. |
| 8,465,530 B2 | 6/2013 | Hammill, Sr. et al. |
| 8,475,501 B2 | 7/2013 | Jackson |
| 8,506,609 B2 | 8/2013 | Biedermann et al. |
| 8,506,611 B2 | 8/2013 | Biedermann et al. |
| 8,518,085 B2 | 8/2013 | Winslow et al. |
| 8,529,604 B2 | 9/2013 | Barker, Jr. et al. |
| 8,556,938 B2 | 10/2013 | Jackson et al. |
| 8,562,652 B2 | 10/2013 | Biedermann et al. |
| 8,617,217 B2 | 12/2013 | Iott et al. |
| 8,628,558 B2 | 1/2014 | Harvey et al. |
| 8,636,769 B2 | 1/2014 | Jackson |
| 8,636,781 B2 | 1/2014 | Biedermann et al. |
| 8,636,782 B2 | 1/2014 | Biedermann et al. |
| 8,663,288 B2 | 3/2014 | Konieczynski et al. |
| 8,663,290 B2 | 3/2014 | Doubler et al. |
| 8,663,291 B2 | 3/2014 | Doubler et al. |
| 8,685,064 B2 | 4/2014 | Hestad et al. |
| 8,709,050 B2 | 4/2014 | Shluzas |
| 8,758,410 B2 | 6/2014 | Heiges et al. |
| 8,764,810 B2 | 7/2014 | Biedermann et al. |
| 8,814,911 B2 | 8/2014 | Jackson |
| 8,845,700 B2 | 9/2014 | Kwak et al. |
| 8,870,927 B2 | 10/2014 | Matthis et al. |
| 8,881,358 B2 | 11/2014 | Biedermann et al. |
| 8,888,827 B2 | 11/2014 | Harper et al. |
| 8,900,270 B2 | 12/2014 | Fauth et al. |
| 8,900,272 B2 | 12/2014 | Jackson |
| 8,926,671 B2 | 1/2015 | Biedermann et al. |
| 8,940,024 B2 | 1/2015 | Biedermann et al. |
| 8,961,568 B2 | 2/2015 | McKinley et al. |
| 8,979,904 B2 | 3/2015 | Jackson et al. |
| 8,986,349 B1 | 3/2015 | German et al. |
| 8,992,579 B1 | 3/2015 | Gustine et al. |
| 8,998,958 B2 | 4/2015 | Dauster et al. |
| 8,998,959 B2 | 4/2015 | Jackson et al. |
| 8,998,960 B2 | 4/2015 | Jackson |
| 8,998,967 B2 | 4/2015 | Biedermann et al. |
| 9,005,259 B2 | 4/2015 | Biedermann et al. |
| 9,017,390 B2 | 4/2015 | Biedermann et al. |
| 9,023,086 B2 | 5/2015 | Biedermann et al. |
| 9,044,273 B2 | 6/2015 | Richelsoph et al. |
| 9,060,814 B2 | 6/2015 | Doubler et al. |
| 9,066,759 B2 | 6/2015 | Biedermann et al. |
| 9,119,674 B2 | 9/2015 | Matthis et al. |
| 9,131,971 B2 | 9/2015 | Biedermann et al. |
| 9,144,444 B2 | 9/2015 | Jackson |
| 9,155,567 B2 | 10/2015 | Auerbach et al. |
| 9,173,684 B2 | 11/2015 | Biedermann et al. |
| 9,186,187 B2 | 11/2015 | Mishra |
| 9,198,694 B2 | 12/2015 | Mishra et al. |
| 9,198,695 B2 | 12/2015 | Shluzas et al. |
| 9,232,969 B2 | 1/2016 | Farris |
| 9,247,965 B2 | 2/2016 | Biedermann et al. |
| 9,254,150 B2 | 2/2016 | Biedermann et al. |
| 9,277,938 B2 | 3/2016 | Biedermann et al. |
| 9,277,941 B2 | 3/2016 | Biedermann et al. |
| 9,277,942 B2 | 3/2016 | Biedermann et al. |
| 9,289,244 B2 | 3/2016 | Hestad et al. |
| 9,289,246 B2 | 3/2016 | Biedermann et al. |
| 9,333,016 B2 | 5/2016 | Biedermann et al. |
| 9,333,017 B2 | 5/2016 | Biedermann et al. |
| 9,339,304 B2 | 5/2016 | Biedermann et al. |

(56) References Cited

U.S. PATENT DOCUMENTS

| | | |
|---|---|---|
| 9,339,320 B2 | 5/2016 | Heiges et al. |
| 9,351,766 B2 | 5/2016 | Biedermann et al. |
| 9,358,047 B2 | 6/2016 | Mishra et al. |
| 9,364,266 B2 | 6/2016 | Biedermann et al. |
| 9,439,680 B2 | 9/2016 | Biedermann et al. |
| 9,451,990 B2 | 9/2016 | Fauth et al. |
| 9,451,991 B2 | 9/2016 | Raju et al. |
| 9,452,006 B2 | 9/2016 | Biedermann et al. |
| 9,453,526 B2 | 9/2016 | Black et al. |
| 9,463,047 B2 | 10/2016 | Raju et al. |
| 9,463,049 B2 | 10/2016 | Konieczynski et al. |
| 9,480,517 B2 | 11/2016 | Jackson et al. |
| 9,486,245 B2 | 11/2016 | Matthis et al. |
| 9,486,246 B2 | 11/2016 | Biedermann et al. |
| 9,492,204 B2 | 11/2016 | Biedermann et al. |
| 9,510,868 B2 | 12/2016 | Biedermann et al. |
| 9,522,021 B2 | 12/2016 | Jackson et al. |
| 9,532,809 B2 | 1/2017 | Biedermann et al. |
| 9,532,810 B2 | 1/2017 | Hestad et al. |
| 9,549,763 B2 | 1/2017 | Harper et al. |
| 9,572,600 B2 | 2/2017 | Biedermann et al. |
| 9,579,125 B2 | 2/2017 | Raju et al. |
| 9,597,119 B2 | 3/2017 | Jackson et al. |
| 9,603,630 B2 | 3/2017 | Farris |
| 9,603,635 B2 | 3/2017 | Leff et al. |
| 9,615,858 B2 | 4/2017 | Doubler et al. |
| 9,649,139 B2 | 5/2017 | Sharifi-Mehr et al. |
| 9,649,142 B2 | 5/2017 | Doubler et al. |
| 9,693,808 B2 | 7/2017 | Fauth et al. |
| 9,707,013 B2 | 7/2017 | Rezach et al. |
| 9,737,338 B2 | 8/2017 | Bazille |
| 9,763,700 B1 | 9/2017 | Gregory |
| 9,788,865 B2 | 10/2017 | Matthis et al. |
| 9,820,780 B2 | 11/2017 | Duncan et al. |
| 9,839,446 B2 | 12/2017 | Biedermann et al. |
| 9,848,916 B2 | 12/2017 | Biedermann et al. |
| 9,883,892 B2 | 2/2018 | Jackson et al. |
| 9,895,170 B2 | 2/2018 | Biedermann et al. |
| 9,895,171 B2 | 2/2018 | Webb |
| 9,907,574 B2 | 3/2018 | Jackson et al. |
| 9,918,745 B2 | 3/2018 | Jackson et al. |
| 9,924,971 B2 | 3/2018 | Biedermann et al. |
| 9,924,975 B2 | 3/2018 | Jackson et al. |
| 9,936,983 B2 | 4/2018 | Mesiwala et al. |
| 9,949,763 B2 | 4/2018 | Rezach |
| 9,949,765 B2 | 4/2018 | Nichols et al. |
| 9,956,003 B2 | 5/2018 | Prevost |
| 9,956,006 B2 | 5/2018 | Jackson |
| 9,962,193 B2 | 5/2018 | Biedermann et al. |
| 9,980,753 B2 | 5/2018 | Jackson et al. |
| 10,022,158 B2 | 7/2018 | Biedermann et al. |
| 10,058,367 B2 | 8/2018 | Biedermann et al. |
| 10,064,659 B2 | 9/2018 | Biedermann et al. |
| 10,076,363 B2 | 9/2018 | Biedermann et al. |
| 10,130,395 B2 | 11/2018 | Leff et al. |
| 10,136,924 B2 | 11/2018 | Konieczynski et al. |
| 10,159,519 B2 | 12/2018 | Biedermann et al. |
| 10,182,848 B2 | 1/2019 | Biedermann et al. |
| 10,188,432 B2 | 1/2019 | Jackson et al. |
| 10,238,430 B2 | 3/2019 | Jackson et al. |
| 10,258,383 B2 | 4/2019 | Biedermann et al. |
| 10,258,384 B2 | 4/2019 | Gregory |
| 10,335,204 B2 | 7/2019 | Matthis et al. |
| 10,357,287 B2 | 7/2019 | Schlaepfer et al. |
| 10,363,073 B2 | 7/2019 | Raina et al. |
| 10,368,916 B2 | 8/2019 | May |
| 10,383,662 B2 | 8/2019 | Biedermann et al. |
| 10,478,229 B2 | 11/2019 | Jackson et al. |
| 10,568,667 B2 | 2/2020 | Biester et al. |
| 10,716,609 B2 | 7/2020 | Biedermann et al. |
| 10,722,272 B2 | 7/2020 | Biedermann et al. |
| 10,729,483 B2 | 8/2020 | Biedermann et al. |
| 10,779,862 B2 | 9/2020 | Biedermann et al. |
| 10,799,272 B2 | 10/2020 | Jackson |
| 10,813,672 B2 | 10/2020 | Jackson et al. |
| 10,856,909 B2 | 12/2020 | Jackson et al. |
| 10,856,911 B2 | 12/2020 | Jackson et al. |
| 10,869,694 B2 | 12/2020 | Jackson et al. |
| 10,918,420 B2 | 2/2021 | Jackson et al. |
| 10,945,768 B2 | 3/2021 | Jackson et al. |
| 10,966,759 B2 | 4/2021 | Gregory |
| 10,980,574 B2 | 4/2021 | Konieczynski et al. |
| 10,987,137 B2 | 4/2021 | Jackson et al. |
| 11,020,150 B1 | 6/2021 | Doubler et al. |
| 11,090,090 B2 | 8/2021 | Biedermann et al. |
| 11,123,109 B2 | 9/2021 | Biedermann et al. |
| 11,147,597 B2 | 10/2021 | Jackson |
| 11,160,582 B2 | 11/2021 | Biedermann et al. |
| 11,219,470 B2 | 1/2022 | Avidano et al. |
| 2003/0060823 A1 | 3/2003 | Bryan |
| 2004/0097933 A1 | 5/2004 | Lourdel et al. |
| 2006/0200131 A1* | 9/2006 | Chao .............. A61B 17/7037 606/328 |
| 2007/0088357 A1 | 4/2007 | Johnson et al. |
| 2007/0090238 A1* | 4/2007 | Justis .............. A61B 17/7038 248/181.1 |
| 2008/0262556 A1 | 10/2008 | Jacofsky et al. |
| 2010/0125302 A1* | 5/2010 | Hammill, Sr. ...... A61B 17/7035 606/301 |
| 2010/0137920 A1 | 6/2010 | Hammill, Sr. et al. |
| 2010/0198272 A1 | 8/2010 | Keyer et al. |
| 2010/0305621 A1* | 12/2010 | Wang .............. A61B 17/7037 606/305 |
| 2011/0118783 A1 | 5/2011 | Winslow et al. |
| 2011/0307018 A1 | 12/2011 | Zucherman et al. |
| 2012/0041490 A1 | 2/2012 | Jacob et al. |
| 2013/0012954 A1 | 1/2013 | Paroth et al. |
| 2013/0046345 A1* | 2/2013 | Jones .............. A61B 17/7086 606/279 |
| 2013/0110180 A1 | 5/2013 | Doubler et al. |
| 2013/0150852 A1 | 6/2013 | Shluzas et al. |
| 2014/0046374 A1 | 2/2014 | Asaad et al. |
| 2014/0257411 A1 | 9/2014 | Rezach |
| 2014/0343617 A1* | 11/2014 | Hannen ............ A61B 17/8605 606/306 |
| 2015/0196337 A1 | 7/2015 | Biedermann et al. |
| 2015/0196338 A1 | 7/2015 | Biedermann et al. |
| 2015/0201972 A1 | 7/2015 | Doubler et al. |
| 2015/0250512 A1 | 9/2015 | Poker et al. |
| 2015/0282844 A1* | 10/2015 | Vedula .............. A61B 17/7032 606/305 |
| 2016/0030086 A1 | 2/2016 | Mishra |
| 2016/0030090 A1 | 2/2016 | Webb |
| 2016/0220277 A1 | 8/2016 | Rezach et al. |
| 2016/0262801 A1* | 9/2016 | Rezach ............ A61B 17/7037 |
| 2017/0020574 A1 | 1/2017 | Biedermann et al. |
| 2017/0049482 A1 | 2/2017 | Campbell et al. |
| 2017/0049484 A1 | 2/2017 | Leff et al. |
| 2017/0065306 A1 | 3/2017 | Fauth et al. |
| 2017/0112542 A1 | 4/2017 | Biedermann et al. |
| 2017/0172630 A1 | 6/2017 | Biedermann et al. |
| 2017/0224386 A1 | 8/2017 | Leff et al. |
| 2017/0245898 A1 | 8/2017 | May et al. |
| 2017/0265903 A1 | 9/2017 | Longtain et al. |
| 2017/0333085 A1* | 11/2017 | Jackson ............ A61B 17/7038 |
| 2018/0014858 A1 | 1/2018 | Biester et al. |
| 2018/0014862 A1 | 1/2018 | Raina et al. |
| 2018/0014863 A1 | 1/2018 | Biester et al. |
| 2018/0021068 A1* | 1/2018 | May .............. A61B 17/7038 606/266 |
| 2018/0036039 A1 | 2/2018 | Biedermann et al. |
| 2018/0055545 A1 | 3/2018 | Biedermann et al. |
| 2018/0092679 A1 | 4/2018 | Toon et al. |
| 2018/0110548 A1 | 4/2018 | May et al. |
| 2018/0116696 A1 | 5/2018 | Hammer et al. |
| 2019/0110817 A1 | 4/2019 | Shluzas et al. |
| 2019/0150989 A1 | 5/2019 | Biester et al. |
| 2020/0038075 A1* | 2/2020 | Barrus .............. A61B 17/7091 |

OTHER PUBLICATIONS

European Search Report issued in Appln. No. 21217539.2 dated Jun. 10, 2022 (2 pages).

(56) References Cited

OTHER PUBLICATIONS

Interational Search Report for PCT/US2021/039063 dated Oct. 13, 2021. (2 pages).
International Search Report issued in Appln. No. PCT/US2022/039395 mailed Jan. 31, 2023 (4 pages).

* cited by examiner

MODULAR HEAD ASSEMBLY FOR SPINAL FIXATION

CROSS-REFERENCE TO RELATED APPLICATIONS

The present application is a continuation-in-part of International Application No. PCT/US2021/059376, filed on Nov. 15, 2021, which claims the benefit of the filing date of U.S. Provisional Patent Application No. 63/115,737, filed on Nov. 19, 2020, the disclosures of which are hereby incorporated herein by reference in their entireties.

BACKGROUND OF THE INVENTION

The present disclosure relates to spinal fixation devices and, more particularly, to modular pedicle fixation assemblies.

The spinal column is a complex system of bones and connective tissues that provides support for the body while protecting the spinal cord and nerves. The spinal column includes a series of vertebral bodies stacked on top of one another, each vertebral body including an inner or central portion of relatively weak cancellous bone and an outer portion of relatively strong cortical bone. Situated between each vertebral body is an intervertebral disc that cushions and dampens compressive forces exerted upon the spinal column, as well as maintains proper spacing of the bodies with respect to each other. A vertebral canal containing the spinal cord and nerves is located behind the vertebral bodies.

There are many types of spinal column disorders including scoliosis (abnormal lateral curvature of the spine), kyphosis (abnormal forward curvature of the spine, usually in the thoracic spine), excess lordosis (abnormal backward curvature of the spine, usually in the lumbar spine) and spondylolisthesis (forward displacement of one vertebra over another, usually in a lumbar or cervical spine), for example, that are caused by abnormalities, such as disease or trauma, and that are characterized by misalignment of the spinal column. When the spinal column is misaligned, one or more of the misaligned vertebral bodies often "pinches" or applies pressure to the underlying spinal cord and nerves, which can result in debilitating pain and diminished nerve function. For this reason, the forgoing conditions regularly require the imposition and/or maintenance of corrective forces on the spine in order to return the spine to its normal alignment.

A surgical technique, commonly referred to as spinal fixation, utilizes surgical implants for fusing together and/or mechanically immobilizing two or more vertebral bodies of the spinal column. Spinal fixation may also be used to alter the alignment of adjacent vertebral bodies relative to one another so as to change the overall alignment of the spinal column.

One common type of spinal fixation device utilizes spinal rods placed parallel to the spine and fixation devices, such as pedicle screw assemblies, interconnected between the spinal rods and selected portions of the spine. In some instances, the spinal rods can then be connected to each other via cross-connecting members to provide a more rigid support and alignment system.

Pedicle screw assemblies typically include a bone screw and a housing or coupling element for coupling the bone screw to the spinal rod. Pedicle screws generally come in two forms: a polyaxial pedicle screw (which allows the housing to freely rotate relative to the screw head) and a uniplanar pedicle screw (which restricts movement of the housing relative to the screw head to a single plane).

Conventional pedicle screws are "top loaded" meaning that assembly of the pedicle screw requires inserting a shank of the bone screw into a proximal end of the housing until the head of the bone screw is retained within the housing and the shank extends from a distal end of the housing. Thus, when securing a conventional pedicle screw to bone, the surgeon must thread the screw into bone while the head of the screw is positioned within the housing.

Despite the improvements that have been made to spinal fixation devices, various drawbacks remain. For example, the housing of a conventional "top loaded" pedicle screw assembly can obstruct a surgeon's vision and/or access while performing operative tasks such as decortication and decompression. This problem is exacerbated by the fact that the housing is subject to "flop" around the head of the screw, which can complicate handling of the pedicle screw assembly, alignment of the housing and fastening of the pedicle screw to bone. Moreover, a surgeon may find it desirable to select between a polyaxial and a uniplanar pedicle screw, based upon various intraoperative considerations, after the screw has been secured to bone. However, switching from a conventional "top loaded" polyaxial pedicle screw to a conventional "top loaded" uniplanar pedicle screw (or vice-versa), after implantation, is not desirable because it requires removal of the previously implanted pedicle screw which can weaken the bone.

BRIEF SUMMARY OF THE INVENTION

Various "bottom loaded" or "modular" pedicle screw assemblies are provided herein. Among other advantages, the distal end of each one of the modular heads is configured to receive the head of the bone screw after the bone screw has been secured to bone. As a result, the surgeon's vision and access is not impaired while performing necessary operative tasks. Moreover, the bone screw defines a feature, such as a groove, designed to selectively engage a corresponding feature, such as a protrusion, provided on select modular head assemblies to restrict movement of the modular head assembly to a single plane relative to the bone screw. Put another way, a kit of differently configured modular head assemblies can include at least one first modular head assembly without the corresponding feature (e.g., the protrusion) and at least one second modular head assembly provided with the corresponding feature. In this manner, a surgeon can select and secure one of the first or second modular head assemblies to the bone screw to create a polyaxial or uniplanar pedicle screw after the bone screw has been implanted into bone and without necessitating removal of the screw from bone. Furthermore, the first and second modular housings may include a biasing member, such as a leaf spring, that provides a constant biasing force to the head of the bone screw and prevents the housing from "flopping" on the screw head which improves handling and alignment of the modular pedicle screw.

One embodiment of the pedicle screw assembly includes a bone screw and a modular head assembly. The bone screw has a head and a shank extending from the head, the head defining at least one groove. The modular head assembly includes a housing and an anvil. The housing has a proximal end and a distal end, and defines a throughbore extending along a longitudinal axis of the housing between the proximal and distal ends. The anvil is disposed within the throughbore. The modular head assembly may include at least one protrusion sized and shaped to be received by the at least one groove for restricting movement of the bone screw to a single plane.

In another embodiment, a spinal fixation kit is provided. The spinal fixation kit includes: a bone screw having a head and a shank extending from the head, the head defining at least one groove; a first modular head assembly and a second modular head assembly. The first modular head assembly including a first housing having a first proximal end and a first distal end, and defining a first throughbore extending between the first proximal and first distal ends; and a first anvil disposed within the first throughbore, wherein the first housing is configured to receive the bone screw and allow the first housing to move in multiple axis relative to the bone screw. The second modular head assembly including a second housing having a second proximal end and a second distal end, and defining a second throughbore extending between the second proximal and second distal ends; and a second anvil disposed within the second throughbore, the second anvil including a protrusion sized to be received by the at least one groove of the bone screw to restrict movement of the second housing relative to the bone screw to a single plane.

In yet another embodiment, a variant spinal fixation kit is provided. The variant spinal fixation kit includes: a bone screw having a head and a shank extending from the head, the head defining at least one groove; a first modular head assembly; and a second modular head assembly. The first modular head assembly includes a first housing having a first proximal end and a first distal end, and defining a first throughbore extending between the first proximal and first distal ends; and a first anvil disposed within the first throughbore, wherein the first housing is configured to receive the bone screw and allow the first housing to move in multiple axis relative to the bone screw. The second modular head assembly includes a second housing having a second proximal end and a second distal end, and defining a second throughbore extending between the second proximal and distal ends; and a second anvil disposed within the second throughbore, the second modular head assembly including a protrusion sized to be received by the at least one groove of the bone screw to restrict movement of the second housing relative to the bone screw to a single plane.

DETAILED DESCRIPTION

As used herein, when referring to the modular pedicle screw assembly, the term "proximal" means the portion of the assembly or a component thereof that is closer to the clinician and the term "distal" means the portion of the assembly or a component thereof that is furthest from the clinician. Also, as used herein, the terms "substantially," "generally," and "about" are intended to mean that slight deviations from absolute are included within the scope of the term so modified.

Figure 1A:
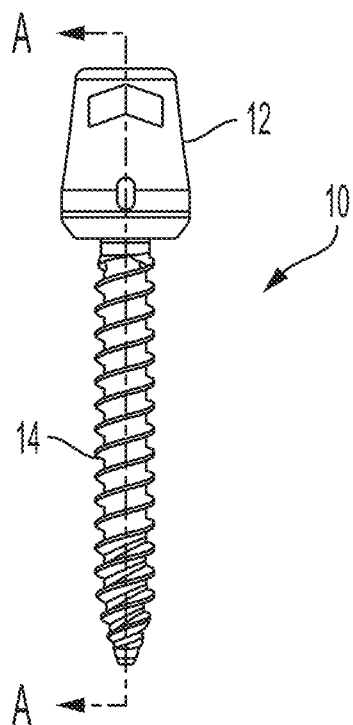
FIG. 1A is a side elevation view of a modular pedicle screw assembly according to an embodiment of the present disclosure.
Figure 1B:
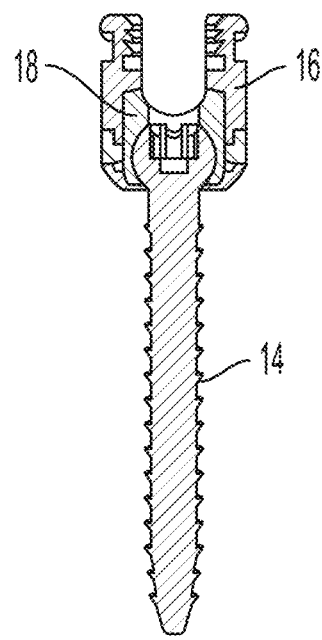
FIG. 1B is a cross section view of the modular pedicle screw assembly taken along line A-A of FIG. 1A.
Figure 1C:
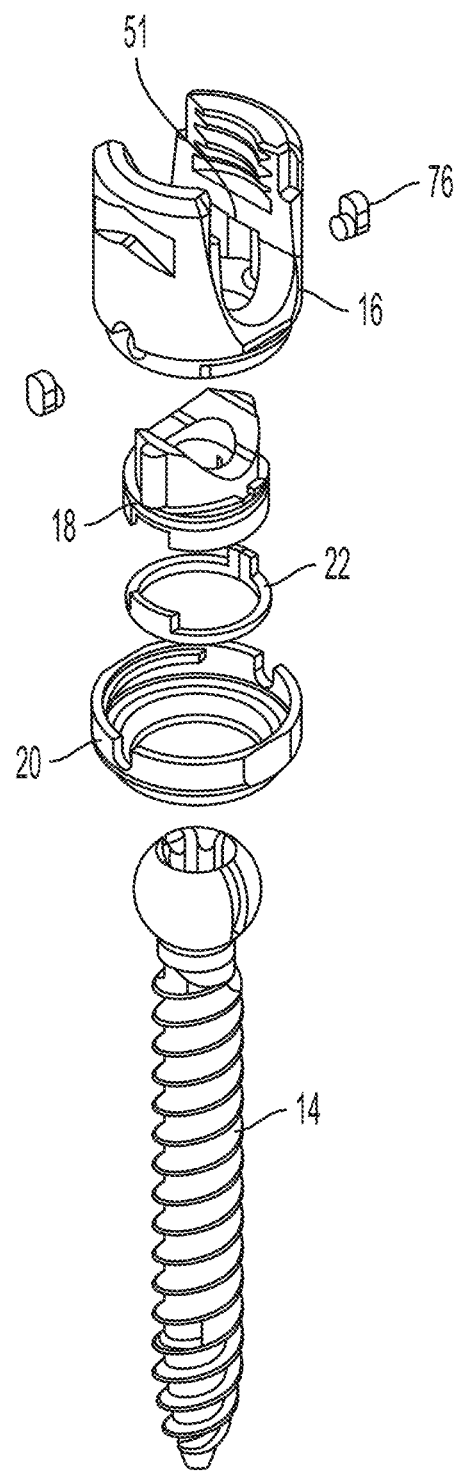
FIG. 1C is an exploded view of the modular pedicle screw assembly of FIGS. 1A and 1B.

FIGS. 1A-1C illustrate a pedicle screw assembly 10 in accordance with an embodiment of the present disclosure. Pedicle screw 10 includes a modular head assembly 12 and a bone screw 14. Modular head assembly 12 is designed such that bone screw 14 can be "bottom loaded" or passed through a distal end of the modular head assembly and fastened to the bone screw after the screw has been implanted in bone.

With reference to FIG. 1C, modular head assembly 12 includes a housing 16, an anvil 18, a cap 20 and a retaining ring 22. Anvil 18 may be a polyaxial anvil 18a, a uniplanar anvil 18b, or a transverse uniplanar anvil 18c (FIGS. 6A-8D). Put differently, the polyaxial anvil 18a, the uniplanar anvil 18b, or the transverse uniplanar anvil 18c may be used in conjunction with housing 16, cap 20 and retaining ring 22 to form modular head assembly 12. When modular head assembly 12 includes polyaxial anvil 18a, the modular head assembly will be permitted to freely rotate (e.g., move in multiple axis) relative to bone screw 14. On the other hand, when uniplanar anvil 18b, or transverse uniplanar anvil 18c are utilized, the movement of modular head assembly 12 will be restricted to a single axis relative to bone screw 14 and, more specifically, an axis in a front-back direction and an axis in a lateral-lateral direction, respectively.

Figure 2A:
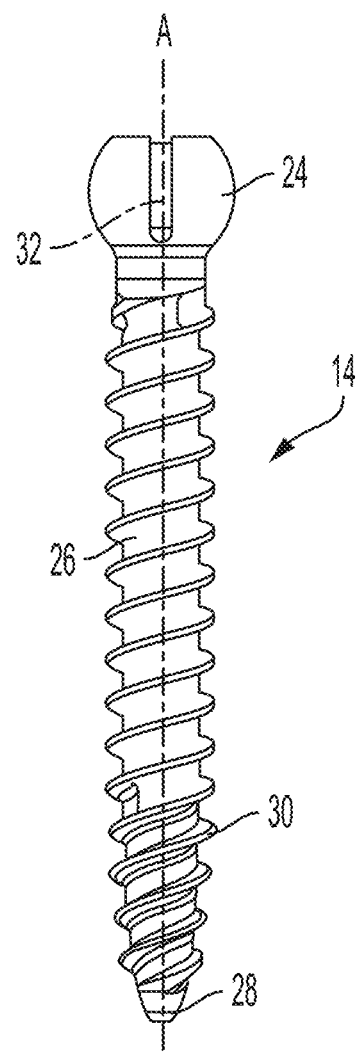
FIGS. 2A and 2B are a side elevation view and a top view, respectively, of a bone screw of the modular pedicle screw assembly of FIGS. 1A-1C.
Figure 2B:
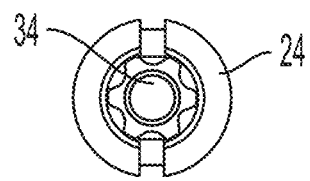
Figure 3A:
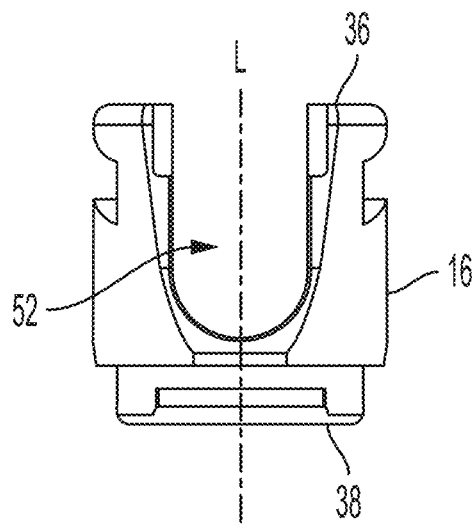
FIGS. 3A-3D are a side elevation view, a front elevation view, a bottom oriented perspective view and a bottom view, respectively, of a housing of the modular pedicle screw assembly of FIGS. 1A-1C.
Figure 3B:
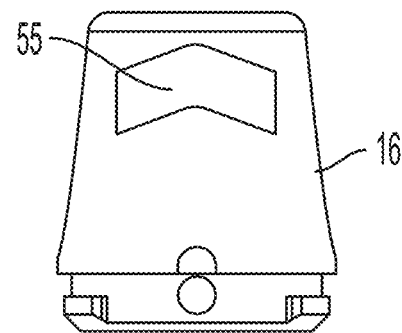
Figure 3C:
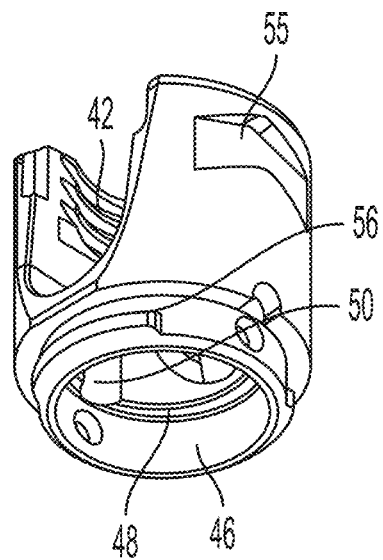
Figure 3D:
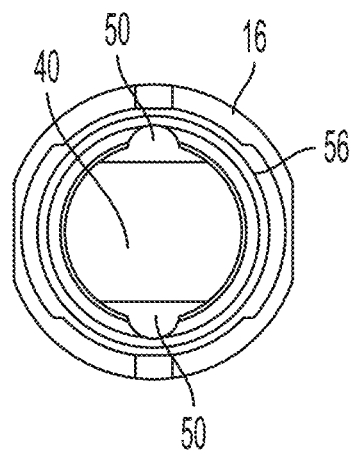
Figure 4A:
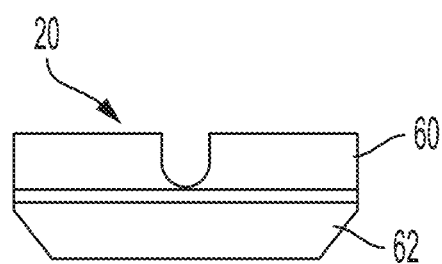
FIGS. 4A-4D are a side elevation view, a front elevation view, a top-oriented perspective view and a bottom view, respectively, of a cap of the modular pedicle screw assembly of FIGS. 1A-1C.
Figure 4B:
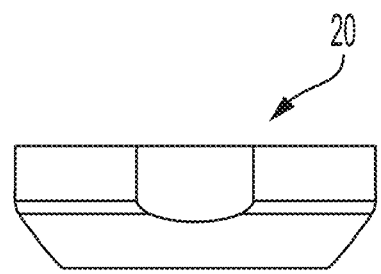
Figure 4C:
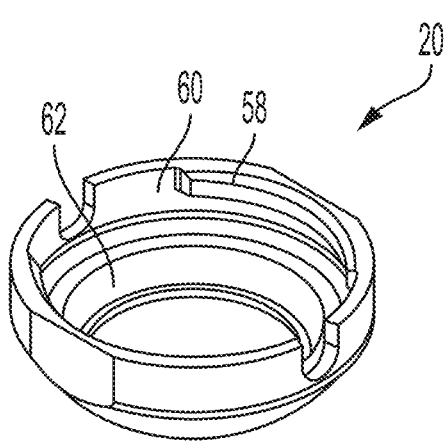
Figure 4D:
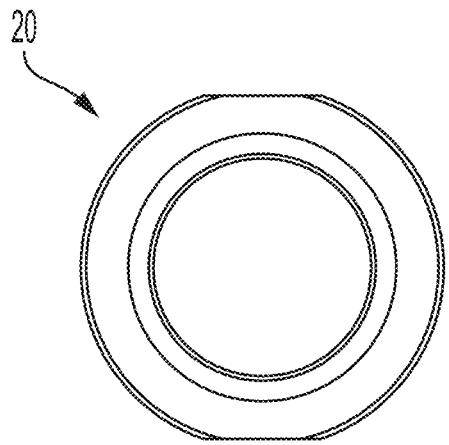
Figure 5A:
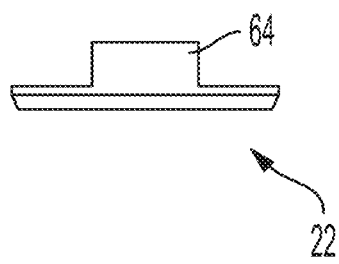
FIGS. 5A-5D is a side elevation view, a front elevation view, a top-oriented perspective view and a bottom view, respectively, of a retaining ring of the modular pedicle screw assembly of FIGS. 1A-1C.
Figure 5B:
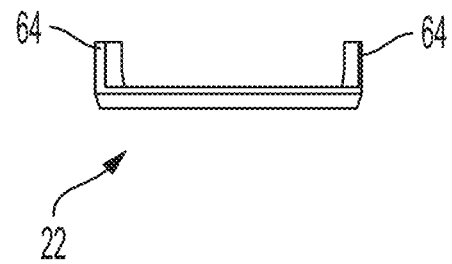
Figure 5C:
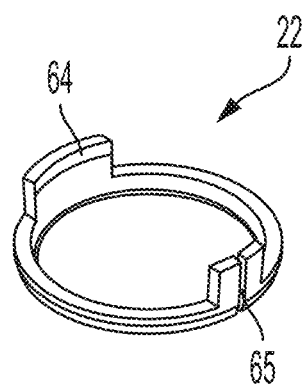
Figure 5D:
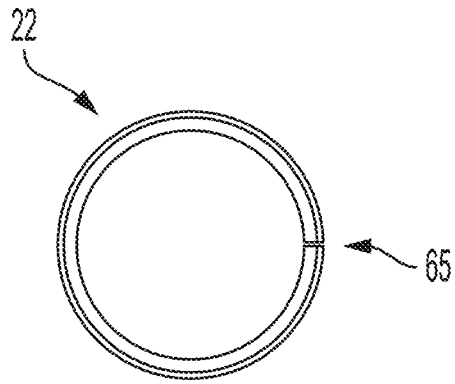

Turning now to FIGS. 2A and 2B, bone screw 14 includes a head 24 provided at a proximal end thereof and a shank 26 extending distally from the head along an axis A. Shank 26 is formed as an elongated body and extends from a distal tip 28 to a proximal end that is coupled (e.g., monolithically formed) to head 24. Distal tip 28 is generally conically-shaped to facilitate insertion of the screw 14 into bone and, in some embodiments, may be self-starting. The elongated body may have a substantially uniform outer diameter upon which a helical thread 30 is provided that allows bone screw 14 to be threadably inserted and retained within bone. Helical thread 30 may be continuous or discontinuous, of uniform or non-uniform pitch, single threaded or double threaded and self-tapping or non-self-tapping depending upon the needs of the procedure being performed. In some embodiments, it is contemplated that the bone screw 14 may be cannulated to permit the passage of a guide wire (not shown) or other instrumentation therethrough. It is also contemplated to provide fenestrations that are fluidly connected to any included cannulation. Such a design may permit the introduction of bone cement or the like after the implantation of the screw within the bone.

The head 24 of bone screw 14 is generally spherical in shape and defines a groove 32 extending in a length direction of the screw between a neck of the screw head and a proximal end of the screw head. Groove 32 is generally aligned with the longitudinal axis A of shank 26 and defines a first lateral wall and a second lateral wall. Thus, when a corresponding feature (e.g., a protrusion) provided on uniplanar anvil 18b or transverse uniplanar anvil 18c (FIGS. 7A-8D) is disposed within groove 32 (e.g., between the first and second lateral walls), the coaction of the corresponding features is designed to restrict movement of modular head assembly 12 to a single plane when the modular head assembly is secured to screw 12. The head 24 of bone screw 14 also defines a tool engaging recess 34 at a proximal portion thereof configured to receive a driving tool (not shown). Tool engaging recess 34 may be any suitable shape capable of transmitting a rotational motion of the tool to the head 24 of bone screw 12. In one non-limiting embodiment, tool engaging recess 34 may be a hexalobe.

Housing 16, as shown in FIGS. 3A-3D, includes a body having a generally cylindrical profile with a proximal surface 36 and an opposite, distal surface 38. Housing 16 defines a throughhole 40 extending along a longitudinal axis L of the body and between the proximal surface 36 and the distal surface 38 of the housing. An inner surface of the proximal portion of the through-hole 40 includes a thread 42 configured to threadably engage a set screw 44 (FIG. 9A) for securing a spinal rod to modular head assembly 12.

A counterbore 46 is formed in the distal surface 38 of housing 16. Counterbore 46 extends towards the proximal surface 36 of housing 16 and terminates at an annular face 48 located at a middle portion of the housing, although it is contemplated that the counterbore may extend any suitable distance from the distal surface. An inner surface of counterbore 46 is formed to have a greater diameter than an inner surface of the proximal portion of throughhole 40 such that anvil 18 can be received therein. An inner surface of throughhole 40 defines a pair of longitudinally extending slots 50 formed in juxtaposed relation to one another. Each slot 50 terminates at a stop 51 (FIG. 1C) and is sized to receive a correspondingly shaped feature on anvil 18 to enable the anvil to slidably translate along the slot and to inhibit rotation of the anvil 18 within throughhole 40.

Figure 9A:
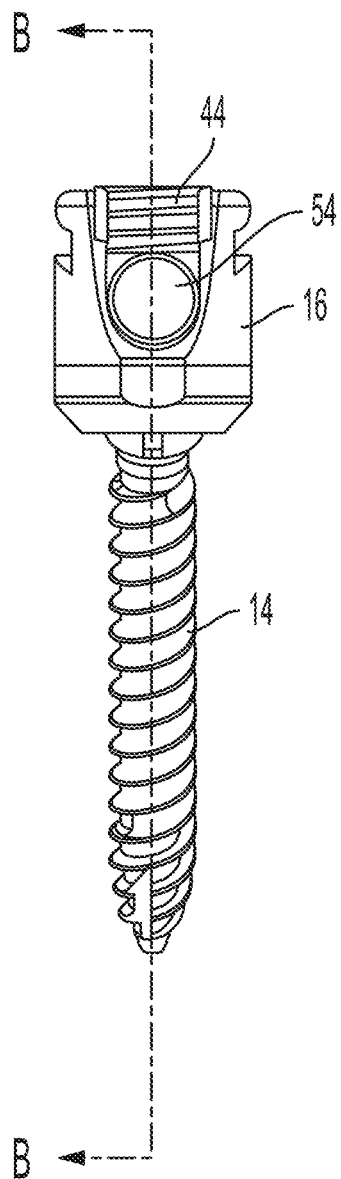
FIG. 9A is a side plan view of an assembled spinal fixation device including a spinal rod, a set screw and the modular pedicle screw assembly of FIGS. 1A-1C.
Figure 9B:
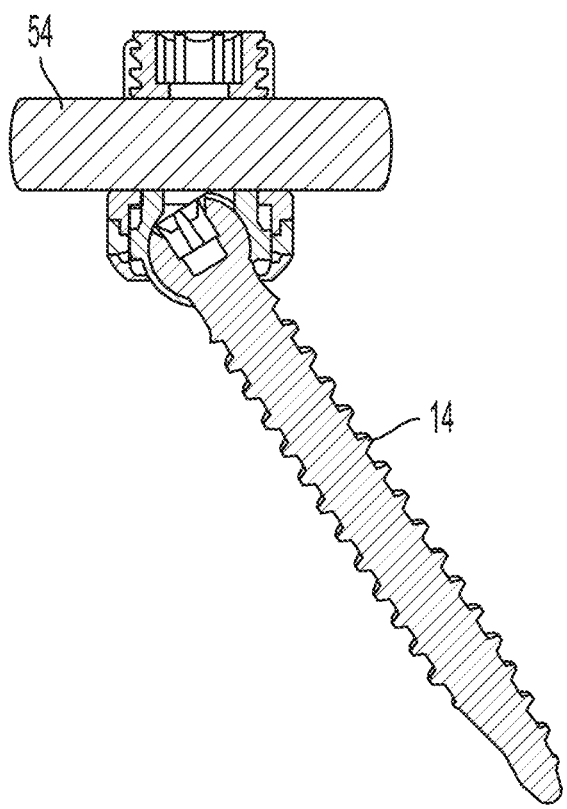
FIG. 9B is a cross section view of the spinal fixation device of FIG. 9A taken along line B-B.

An outer surface of housing 16 defines a U-shaped opening 52 extending through the proximal surface 36 of the body and transverse to throughhole 40. U-shaped opening 52 is configured to receive spinal rod 54 (FIGS. 9A and 9B). Two reliefs 55 are formed in the outer surface of housing 16. The reliefs 55 are configured to receive a suitable tool (not shown) and enable a clinician to grasp and manipulate housing 16 during a surgical procedure. An outer surface of the distal portion of housing 16 includes a thread 56 or flange for coupling the housing to cap 20. Housing 16 may be formed from any biocompatible material suitable for use in surgical procedures, such as metallic materials including titanium, titanium alloys, stainless steels, cobalt chrome alloys, etc., or non-metallic materials such as ceramics, polyetheretherketone (PEEK), etc.

Assembly cap 20, shown in FIGS. 4A-4D, includes a corresponding discontinuous thread 58 or flange for engaging the thread 56 on housing 16 in order to facilitate assembly of modular head assembly 12. Assembly cap 20 forms a retaining ring receiving portion defined by a proximal portion 60 and a distal portion 62. An interior surface of the distal portion 62 is tapered inwardly from the proximal portion 60 to a distal end of assembly cap 20. As a result, the retaining ring receiving portion is configured to slidably receive retaining ring 22 as will be described in further detail hereinbelow.

Referring to FIGS. 5A-5D, retaining ring 22 has a ring shaped body with two arms 64 extending proximally from an upper surface of the cylindrical body. The arms 64 of retaining ring 22 are sized to fit within a gap of discontinuous thread 58 allowing the retaining ring to slidably translate within the retaining ring receiving portion of cap 20 and to inhibit rotation of the retaining ring within the retaining ring receiving portion.

Retaining ring 22 is formed of an elastic material, such as an elastic metal, and defines a slit 65 extending therethrough from an outer surface of the cylindrical body to the inner surface of the cylindrical body. In this manner, retaining ring 22 is configured to expand and compress upon the application of an external force (e.g., a compressive force applied to an outer surface of the cylindrical body) or upon the application of an internal force (e.g., an expansion force applied to an inner surface of the cylindrical body). In this regard, retaining ring 22 is designed to transition between an expanded configuration in which the retaining ring is sized to receive the head 24 of bone screw 14 and a compressed configuration in which the retaining ring prevents the head of the bone screw from passing distally through the retaining ring.

When the head 24 of bone screw 14 is passed through the distal end of cap 20 (e.g., bottom loaded) and into engagement with retaining ring 22, the head of the bone screw forces the retaining ring to slide proximally within the retaining ring receiving portion. When retaining ring 22 is disposed within the larger proximal portion 60 of the retaining ring receiving portion, an internal force applied by the head 24 of bone screw 14 forces the retaining ring to expand to a diameter greater than its natural configuration and allows the head of the screw to pass proximally through the retaining ring. After the head 24 of bone screw 12 has passed through retaining ring 22, the retaining ring will elastically transition back to its natural configuration around the neck (e.g., the junction of the proximal portion of shank 26 and the head) of the bone screw. Conversely, when set screw 44 is threaded distally into housing 16, the set screw applies a distally directed force which causes retaining ring 22 to translate from the proximal portion 60 of the retaining ring receiving portion into the distal portion 62 of the retaining ring receiving portion. As a result, the tapered surface of the distal portion 62 of the retaining ring receiving portion applies a compressive force on the outer surface of retaining ring 22 and causes the retaining ring to compress around the neck of bone screw 14 to a diameter less than then the diameter of the retaining ring in its natural configuration. The reduced diameter of retaining ring 22 prevents the head 24 of screw 14 from passing distally through modular head assembly 12.

Referring to FIGS. 6A-6D, polyaxial anvil 18a has a body that is sized to be slidably received within the throughbore 40 of housing 16. The body of polyaxial anvil 18a has a proximal surface 68 that defines a concave profile (e.g., extending toward a distal surface 70 of the body) configured to receive a portion of the spinal rod 54 (FIGS. 9A and 9B). An outer surface of polyaxial anvil 18a includes a pair of lugs 66 diametrically opposed from one another about the body. Each one of the lugs 66 extends in the longitudinal direction and is sized to be is received within a corresponding slot 50 of housing 16 to guide the sliding movement of the polyaxial anvil within throughhole 40 and to inhibit rotation of the anvil relative to the housing. In this manner, engagement between the lugs 66 of anvil 18a and the slots 50 of housing 16 ensure that the concave proximal surface of the anvil remains aligned with the U-shaped opening 52 of the housing in order to receive spinal rod 54. The distal surface 70 of polyaxial anvil 18a defines a concave profile (e.g., extending toward the proximal surface 68 of the anvil). The concave profile of the distal surface 70 of polyaxial anvil 18a generally corresponds in shape to the spherical head 24 of bone screw 14 thus allowing modular head assembly 12 to freely rotate in multiple directions about the head of the screw. For this reason, the distal surface 70 of polyaxial anvil 18a is sometimes referred to herein as the "contact surface."

Figure 6A:
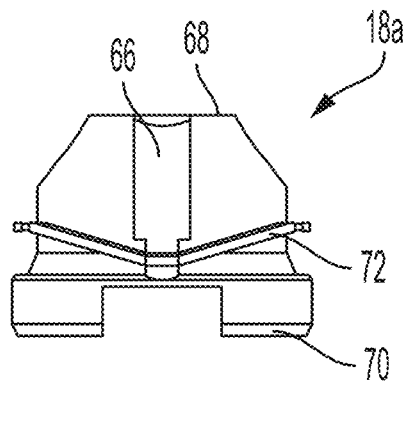
FIGS. 6A-6D is a side elevation view, a front elevation view, a bottom-oriented perspective view and a bottom view, respectively, of a polyaxial anvil for use in the modular pedicle screw assembly of FIGS. 1A-1C.
Figure 6B:
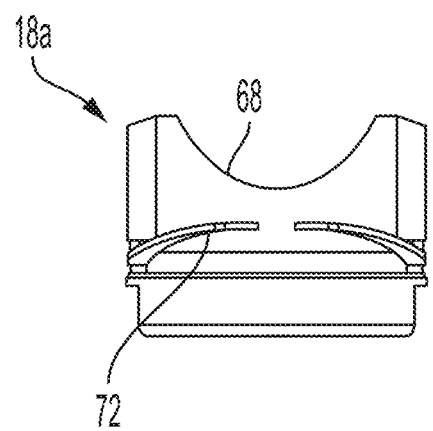
Figure 6C:
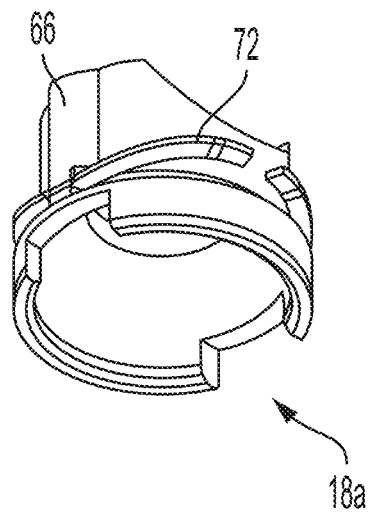
Figure 6D:
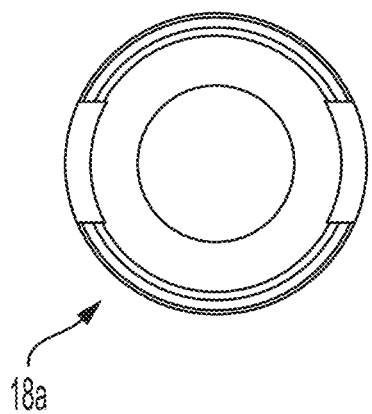
Figure 7A:
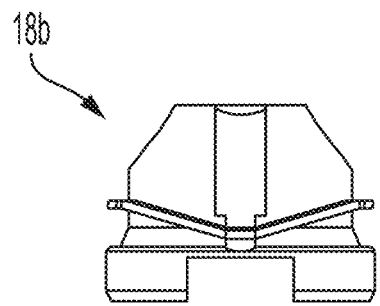
FIGS. 7A-7D is a side elevation view, a front elevation view, a bottom-oriented perspective view and a bottom view, respectively, of a uniplanar anvil for use in the modular pedicle screw assembly of FIGS. 1A-1C.
Figure 7B:
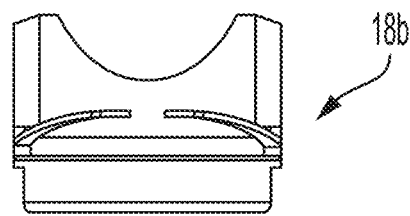
Figure 7C:
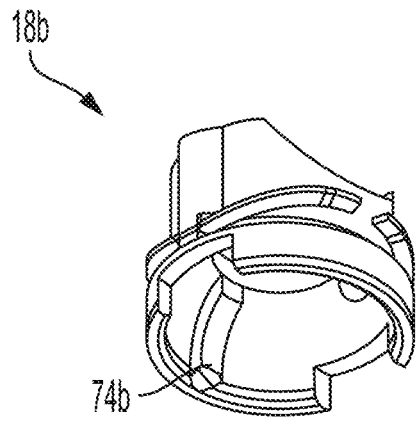
Figure 7D:
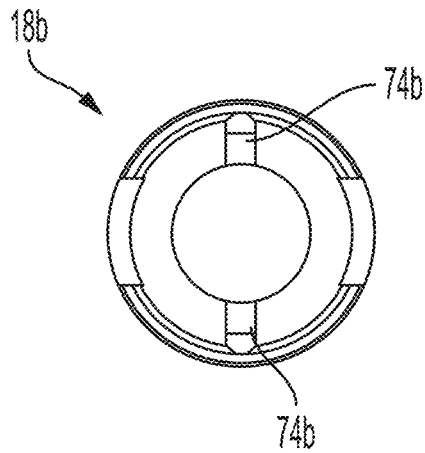
Figure 8A:
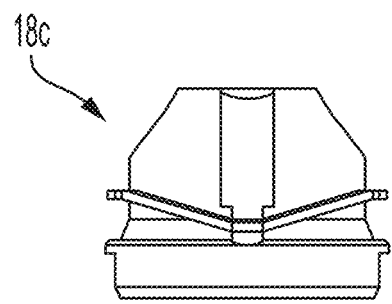
FIGS. 8A-8D is a side elevation view, a front elevation view, a bottom-oriented perspective view and a bottom view, respectively, of a transverse uniplanar anvil for use in the modular pedicle screw assembly of FIGS. 1A-1C.
Figure 8B:
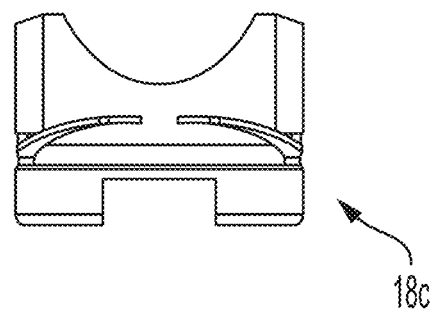
Figure 8C:
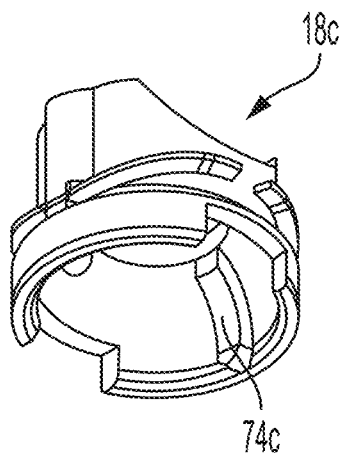
Figure 8D:
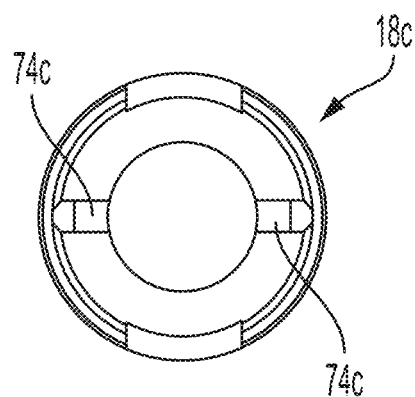

A plurality of leaf springs 72 are attached to and at least partially circumscribe the outer surface of polyaxial anvil 18a. Leaf springs 72 are thus positioned to engage the annular face 48 of counterbore 46. As a result, when the head 24 of bone screw 14 is bottom loaded through retaining ring 22 and into engagement with the contact surface of the bone screw, leaf springs 72 impart a biasing force to the bone screw. This biasing force ensures that the contact surface of polyaxial anvil 18a applies a constant distally directed force against the head of the bone screw and prevents modular head assembly 12 from "flopping" loosely about the head of the bone screw. As a result, the biasing force affords the clinician greater control while securing modular head assembly 12 to bone screw 24. The fact that leaf springs 72 are attached to (or monolithically formed with) polyaxial anvil 18a facilitates efficient assembly of modular head assembly 12 as the springs do not need to be aligned and loaded within housing 16 separately from the anvil. As shown in FIG. 6D, a bore is defined along a longitudinal axis of polyaxial anvil 18a and between the proximal and distal ends of the anvil.

Uniplanar anvil 18b, as shown in FIGS. 7A-7D, is substantially similar to polyaxial anvil 18a except that the uniplanar anvil additionally includes a pair of longitudinally aligned protrusions 74b provided on the contact surface of the uniplanar anvil. Each protrusion 74b is diametrically opposed about the bore from the other protrusion and spaced 90 degrees from each one of the lugs 66. Protrusions 74b are sized and shaped to be positioned within the groove 32 defined in the head 24 of bone screw 14. In this regard, when the groove 32 of bone screw 14 receives the protrusion 74b of uniplanar anvil 18b, movement of modular head assembly 12 relative to the bone screw is restricted to a single plane (e.g., the plane along which the protrusion extends).

Transverse uniplanar anvil 18c is shown in FIGS. 8A-8D. Transverse uniplanar anvil 18c is formed substantially similar to uniplanar anvil 18b but for the location of protrusions 74c. That is, the protrusions 74c of transverse uniplanar anvil 18c are rotated 90 degrees about the contact surface relative to the protrusions 74b of uniplanar anvil 18b. The protrusions 74c of anvil 18c are thus configured to restrict relative movement between the modular head assembly 12 and bone screw 14 a single plane extending orthogonal to the U-shaped opening 52 of housing 16.

A spinal fixation kit is also provided herein. The spinal fixation kit includes, inter alia, one or more modular head assemblies 12, one or more bone screws 14, one or more spinal rods 54 and one or more set screws 44. Each of the one or more modular head assemblies 12 may be similarly configured, such that they contain the same anvil, or differently configured, such that the anvils have different configurations. For example, the spinal fixation kit may include at least one modular head assembly utilizing a polyaxial anvil 18a, at least one modular head assembly utilizing a uniplanar anvil 18a and at least one modular head assembly utilizing a transverse uniplanar anvil 18c. In this regard, the clinician can determine whether to attach a polyaxial, uniplanar or transverse uniplanar modular head to a previously implanted bone screw 14 based upon intraoperative considerations.

FIGS. 9A and 9B illustrate modular pedicle screw 10 in an assembled state. Irrespective of whether modular head 12 is formed with a polyaxial anvil 18a, a uniplanar anvil 18b, or a transverse uniplanar anvil 18c, the modular head is assembled in the same manner. For this reason, the following description of the assembly of the modular head refers to the anvil generically as anvil 18.

Modular head 12 is assembled by aligning the lugs 66 of anvil 18 with the corresponding slots 50 of housing 16. Once lugs 66 are in alignment with slots 50, the anvil is proximally advanced into counterbore 46 until leaf springs 72 engage the annular face 48 of the counterbore. Next, retaining ring 22 is inserted into the retaining ring receiving portion of assembly cap 20 such that the arms 64 of the retaining ring are positioned within a gap of the discontinuous thread 58 on assembly cap 20 and a lower surface of the body of the retaining ring is positioned within the distal portion 62 of the assembly cap. The thread 58 on assembly cap 20 is then threaded to the thread 56 disposed on the distal end of housing 16 to threadably secure the cap to the housing. In some embodiments, as shown in FIG. 1C, pedicle screw 10 may also include assembly pins 76 which are inserted through apertures in the distal portion of housing 16 and welded to the housing to secure assembly cap 20 to the housing. It will be appreciated, however, that assembly of modular head 12 need not include the step of welding assembly pins 76 to housing 16. Instead, cap 20 may be secured to housing 16 only by coupling the threads 58 on the cap to the thread 56 on the housing or via another known coupling mechanisms. In this regard, it is contemplated that a manufacturer can assemble modular head 12 before shipping the modular head to the end user, or alternatively, an end user could assemble the modular head before use.

Use of pedicle screw 10 to fixate spinal rod 54 will now be described. Bone screw 14 is first driven into bone using a driving tool (not shown) by inserting a working end of the driving tool into the tool engaging recess 34 of the screw and rotating the driving tool to thread the screw into bone. With the bone screw 14 secured at a desired location, the surgeon may select one of the polyaxial, uniplanar or transverse uniplanar head assemblies to couple to the screw in view of intraoperative considerations including the exact placement and orientation of the screw(s) and the desired placement of the spinal rod 54. Because each one of the polyaxial, uniplanar and transverse uniplanar modular head assemblies are secured to screw 14 in a substantially similar manner, a single generic description of the coupling will be described hereinafter such that specific descriptions of the polyaxial, uniplanar and transverse uniplanar modular head assemblies are only set forth when describing contrasting features between the modular assemblies.

With the selected modular head assembly 12 in hand, the modular head assembly may be placed adjacent the head 24 of screw 14 and advanced in a distal direction over the head of the bone screw. As the head 24 of bone screw 14 is advanced proximally within throughbore 40, the head of the bone screw contacts retaining ring 22 and forces the retaining ring and anvil 18 to translate in a proximal direction and from the distal portion 62 of cap 20 into a proximal portion 60 of the cap. The interaction of the lugs 66 of anvil 18 and the slots 50 of housing 16 guides movement of the anvil within throughbore 40 as the anvil slides in the proximal direction until the proximal end 68 of the anvil engages the stop 51 of the slot. With anvil 18 pressed against stop 51, continued application of a distally directed force on modular head 12, will force the head 24 of bone screw 14 through retaining ring 22 and into contact with the concave, distal surface 70 of anvil 18. Specifically, the spherical shape of the head 24 of bone screw 14 will place an outwardly directed force on an interior surface of retaining ring 22 and causes the elastic retaining ring to transition from a natural configuration to an expanded (e.g., larger diameter) configuration allowing the head of the bone screw to pass completely though the aperture of the retaining ring. It will be appreciated that retaining ring 22 is permitted to expand to the expanded configuration, in part, because the retaining ring is disposed within the larger, proximal portion 60 of the retaining ring receiving portion of cap 20. Once the head 24 of bone screw 14 has completely passed through retaining ring 22, the retaining ring will elastically return to its natural size about the neck of bone screw 14.

If modular head assembly 12 includes a polyaxial anvil 18a, the spherically shaped head 24 of bone screw 14 will be permitted to freely rotate about the concave distal surface 70 of the anvil in multiple directions relative to the bone screw. In contrast, if modular head assembly 12 includes a uniplanar anvil 18b or a transverse uniplanar anvil 18c, engagement between the groove 32 of screw 14 and the protrusion 74b, 74c of uniplanar anvil or transverse uniplanar anvil, respectively, will restrict movement of the modular head assembly to a single axis relative to the bone screw. More particularly, the uniplanar anvil will restrict movement of the housing in a front-back direction while the transverse uniplanar anvil will restrict movement of the housing in a lateral-lateral direction (e.g., orthogonal to the front-back direction).

When modular head 12 is coupled to bone screw 14, the leaf springs 72 of anvil 18 contact the annular face 48 of counterbore 46 and impart a biasing force on the bone screw which ensures that the contact surface of the anvil applies a constant distal pressure to the head 24 of bone screw 14. The biasing force prevents modular head assembly 12 from "flopping" loosely about the head of the screw. In this regard, modular head assembly 12 is held in place relative to screw 14 such that the surgeon has to apply a rotational force to the modular head assembly in order to reposition the modular head assembly relative to the bone screw. As a result, the biasing force affords the clinician greater control and the ability to make minor adjustments in the position of the modular head assembly relative to the screw.

Referring now to FIGS. 9A and 9B, spinal rod 54 may then be interconnected between adjacent modular head assemblies by inserting the spinal rod within the U-shaped openings 52 of each housing 16 and within the concave relief of the proximal surface 68 of anvil 18. Using a driving tool, the surgeon may then thread set screw 44 into the threads 42 of housing 16, which in turn, forces spinal rod 54, anvil 18 and retaining ring 22 in a distal direction within the counterbore 40 of the housing. Distal translation of anvil 18 urges retaining ring 22, along with the bone screw 14 captured therewithin, to translate into the distal portion 62 of the retaining ring receiving portion of cap 20. The tapered sidewall and smaller diameter of the distal portions 62 of cap 20 imparts an inwardly directed force on an outer surface of retaining ring 22 and causes the retaining ring to compress and clamp around the neck of bone screw 14, thereby fixing the rotational and angular position of the bone screw relative to housing 16 and preventing the bone screw from passing through a distal end of the housing.

Figure 10:
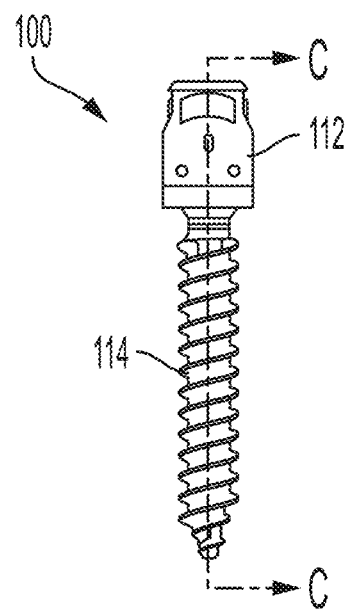
FIG. 10 is a side elevation view of a modular pedicle screw assembly according to another embodiment of the present disclosure.
Figure 11:
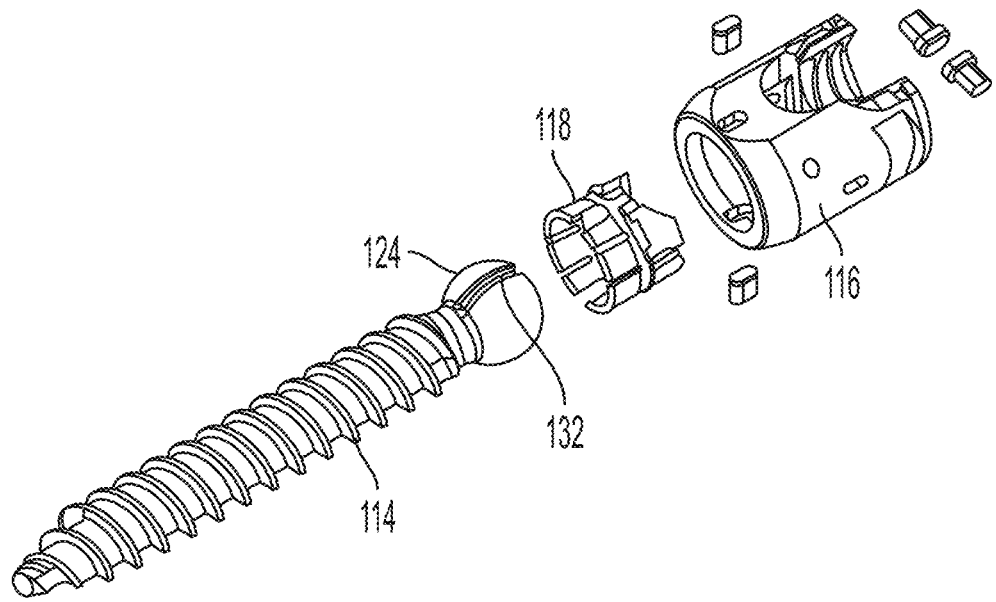
FIG. 11 is an exploded view of the pedicle screw assembly of FIG. 10.

FIGS. 10 and 11 illustrate a modular pedicle screw assembly 100 in accordance with another embodiment of the present disclosure. Pedicle screw 100 includes a bottom loading modular head assembly 112 and a bone screw 114.

Figure 15A:
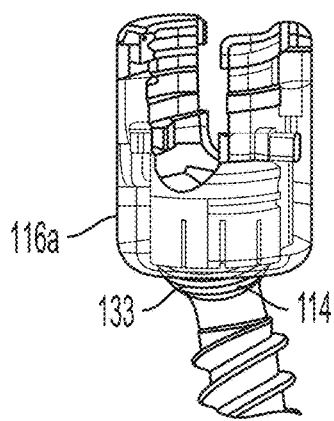
FIGS. 15A-15C are perspective views of a polyaxial housing, a uniplanar housing and a transverse uniplanar housing, respectively, of the pedicle screw assembly of FIG. 10.
Figure 15B:
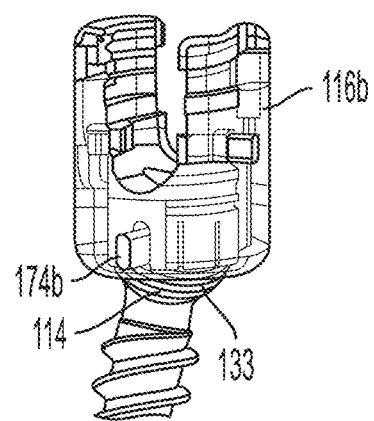
Figure 15C:
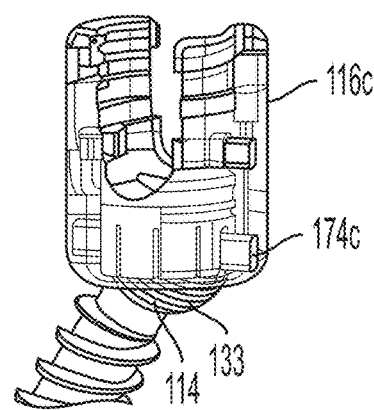

Bone screw 114 is substantially similar to previously described bone screw 14 (FIGS. 2A and 2B) and, for brevity, is not described again in detail hereinafter. Instead, when like features are referenced in connection with bone screw 114, the previously described features will be renumbered with sequential one hundred series numerals. In some embodiments, however, bone screw 114 may additionally define a series of friction enhancing notches 133 that extend about the head 124 of the bone screw in a circumferential direction as illustrated in FIGS. 15A-15C. Circumferential notches 133 are designed to cooperate with features on the anvil to create friction so that modular head assembly 112 is poseable and to also assist in retaining screw 114 within the modular head assembly.

Modular head assembly 112 includes a housing 116 and an anvil 118. Unlike modular head assembly 12 (which relies on the absence or presence of a protrusion on the anvil), modular head assembly 112 relies on the absence or presence of a protrusion extending through or from on a polyaxial housing 116a, a uniplanar housing 116b or a transverse uniplanar housing 116c for performing the same function.

As shown in FIGS. 11, 13, 14 and 15A-15C, polyaxial housing 116a, uniplanar housing 116b, and transverse uniplanar housing 116c are substantially the same as one another but for the presence and/or location of the protrusion. For this reason, a single description of the housing is set forth below with the housing generically referenced by numeral 116. Housing 116 includes a body having a generally cylindrical profile with a proximal surface 136 and an opposite, distal surface 138. Housing 116 defines a through-hole 140 extending along a longitudinal axis L' of the body and between the proximal surface 136 and the distal surface 138 of the housing. An inner surface of the proximal portion of the through-hole 140 includes threading 142 configured to threadably engage a set screw for securing a spinal rod to modular head assembly 112.

The distal surface 138 of housing 116 defines a counterbore 146 having a greater diameter than an inner surface of the proximal portion of throughhole 140 such that anvil 118 can be received therein. Counterbore 146 extends towards the proximal surface 136 of housing 116 and terminates at a middle portion of the housing. A pair of lugs 166 extend through an aperture formed through the sidewall of housing 116 and into counterbore 146. Each one of lugs 166 are spaced 180 degrees about the inner surface of throughbore 140 from the other lug and configured to engage a corresponding feature, such as a slot on anvil 118, to allow the anvil to slidably translate within throughbore 140 and to inhibit rotation of the anvil within the throughbore. It will be appreciated, however, that lugs 166 may extend from an inner sidewall of housing 116 instead of extending therethrough.

Counterbore 146 forms an anvil retaining space having a proximal portion 160 and a distal portion 162. An inner surface of distal portion 162 is tapered inwardly from proximal portion 160 to the distal surface 162 of housing 116. As a result, anvil 118 is configured to slide within counterbore 146 and to receive and clamp bone screw 114 as described below. The inner surface of proximal portion 160 defines a series of detents 147 annularly spaced about the inner surface of counterbore 146 for temporarily securing anvil 118 thereby preventing the anvil from sliding within the counterbore until the anvil is forced from the detent.

The outer surface of housing 116 defines a U-shaped opening 152 extending through the proximal surface 136 of the body and transverse to throughhole 140. As a result, U-shaped opening 152 is configured to receive a spinal rod. Two reliefs 155 are formed in the outer surface of housing. The reliefs 155 are configured to receive a suitable tool (not shown) and enable a clinician to grasp and manipulate housing 116 during a surgical procedure.

Figure 12:
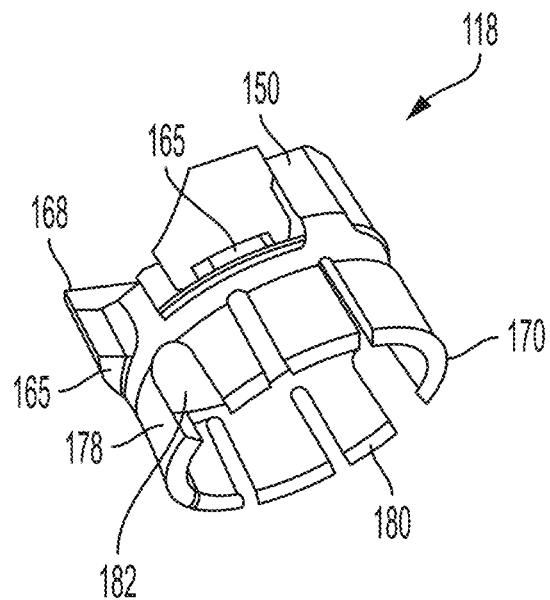
FIG. 12 is a perspective view of an anvil of the modular pedicle screw assembly FIGS. 10 and 11.
Figure 13:
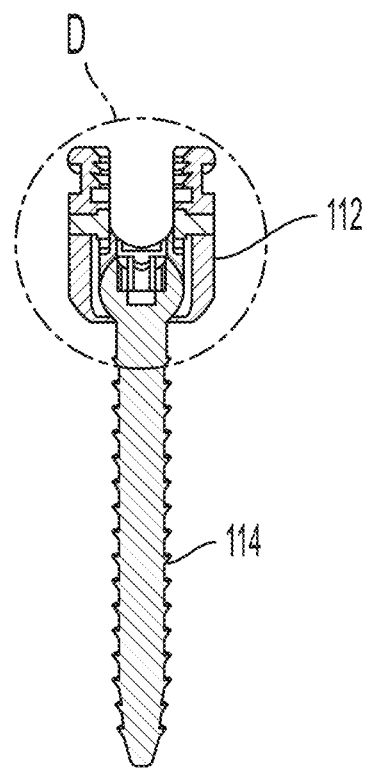
FIG. 13 is a cross section view of the pedicle screw assembly of FIG. 10 taken along line C-C.
Figure 14:
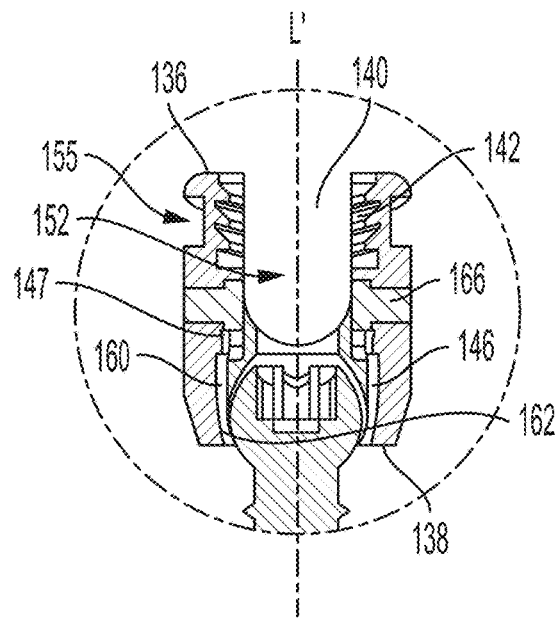
FIG. 14 is an enlarged view of section D of FIG. 13.

Anvil 118, as shown in FIG. 12, has a body that is sized to be slidably received within counterbore 146 of housing 116. The body of 118 has a proximal surface 168 that defines a concave profile (e.g., extending toward a distal surface 170 of the body) such that it is configured to receive a spinal rod. A pair of diametrically opposed slots 150 are defined through the outer surface of the proximal portion of anvil 118. Each slot 150 extends in the longitudinal direction and is sized to receive the lugs 166 of housing 116 to guide the sliding movement of anvil 118 within counterbore 146 and to inhibit rotation of the anvil relative to housing 116. In this regard, the lugs 166 of housing 116 and the slots 150 of anvil 118 coact to ensure that the concave relief of the anvil remains aligned with the U-shaped opening 152 of the housing to receive a spinal rod. The outer surface of anvil 118 includes a series of ledges 165 annular spaced about the anvil. The ledges 165 are correspondingly shaped to be received by the detents 147 of housing 116 and allow the housing to temporarily secure anvil 118 within a proximal portion of counterbore 146 when the ledges of the anvil are disposed within the detents.

The distal surface 170 of anvil 118 defines a concave surface (e.g., extending toward the proximal surface 168 of the anvil). The concave profile of the distal surface 170 of anvil 118 generally corresponds in shape to the spherical head 124 of bone screw 114 thus allowing modular head assembly 112 to freely rotate in multiple directions about the head of the bone screw unless otherwise prevented by another feature.

Anvil 118 further includes a plurality of flanges 178 annularly spaced about a perimeter of the anvil and extending from the distal surface 170 in a distal direction. The plurality of flanges 178 collectively form a receiving cavity for receiving the head 124 of bone screw 112. Each one of the plurality of flanges 178 is formed of a flexible and resilient material that allows the flange to flex outwardly and inwardly and then to return to its natural configuration (e.g. parallel to the longitudinal axis of the anvil). Thus, flanges 178 are flexibly moveable between an outwardly flexed or expanded configuration in which the receiving cavity is sized to receive the head 124 of the bone screw 114 and an inwardly flexed or compressed configuration in which the flanges clamp the head of the screw to lock the screw in position and prevent the screw from passing distally through the distal surface 138 of housing 116.

The clamping of the head 124 of bone screw 114 is assisted by an inwardly extending lip 180 provided at a distal end of each one of the flanges 178. The lips 180 are configured to engage the circumferential notches 133 of bone screw 114 to more securely clamp the screw. Adjacently spaced flanges form a gap 182 that allows protrusion 174b, 174c to extend therethrough and into a groove 132 of bone screw 114.

With specific reference to FIGS. 15A-15C, a polyaxial housing 116a, a uniplanar housing 116b, or a transverse uniplanar housing 116c may be used in conjunction with anvil 118 to form a polyaxial modular head assembly, a uniplanar modular head assembly, or a polyaxial modular head assembly, respectively. Polyaxial housing 116a is devoid of protrusions capable of engaging the head 124 of bone screw 114 and, as a result, the polyaxial head is permitted to freely rotate (e.g., move in multiple axis) relative to the bone screw. On the other hand, protrusion 174b extends through an aperture formed in the distal portion of uniplanar housing 116b, through the gap 182 formed between adjacent flanges 178 and into the groove 132 of bone screw 114 to restrict rotation of the housing to a single axis (e.g., front-back relative to the U-shaped opening 152 of the housing) relative to the bone screw. Similarly, a protrusion 174c extends through an aperture formed in the distal portion of housing 116c, through the gap 182 formed between adjacent flanges 178 and into the groove 132 of bone screw 114 to restrict rotation of the housing to a single axis relative to the bone screw (e.g., lateral-lateral relative to the U-shaped opening 152 of the housing).

A spinal fixation kit formed of various modular head assemblies 112 is also contemplated. The spinal fixation kit includes one or more modular head assemblies 112, one or more bone screws 114, one or more spinal rods and one or more set screws. Each of the one or more modular head assemblies 112 may be similarly configured, such that they contain the same housing, or differently configured, such that the housings have different configurations. For example, the spinal fixation kit may include at least one modular head assembly including polyaxial housing 116a, at least one modular head assembly including uniplanar housing 116b and at least one modular head assembly including transverse uniplanar housing 116c. In this regard, the clinician can determine which modular head assembly to secure to a previously implanted bone screw 114 based upon intraoperative considerations and after the bone screw has been implanted.

Use of pedicle screw 100 to fixate a spinal rod will now be described. Bone screw 114 is first driven into bone at a desired location. The surgeon may then select one of the polyaxial, uniplanar or transverse uniplanar modular head assemblies to couple to the bone screw in view of intraoperative considerations including the exact placement and/or orientation of the bone screw(s) and the desired placement of the spinal rod.

Modular head assembly 112 may then be advanced in a distal direction over the head 124 of bone screw 114 such that the head of the bone screw is advanced proximally within throughbore 140 and into contact with the lips 180 of flanges 178. The interaction between the ledges 165 of anvil 118 and the detents 147 of counterbore 146 prevents the anvil from translating relative to housing 116. Continued application of a distally directed force on modular head 112 will forces the head 124 of bone screw 114 into the receiving cavity of anvil 118 and into contact with the concave distal surface 170 of the anvil. More particularly, the spherically shaped bone screw head places an outwardly directed force on the lips 180 of flanges 178 and causes each of the flanges to flex outwardly such that the receiving cavity expands in diameter and allows the head 124 of bone screw 114 to be received therein. Once the largest diameter of the head 124 of bone screw 114 has passed over the lips 180 of flanges 178, the flanges will elastically return to their natural configuration and the lips will engage the circumferential notches 133 formed on the bone screw head to secure the head within the cavity. It will be appreciated that flanges 178 are permitted to flex, in part, because the flanges are disposed within the larger, proximal portion 160 of the counterbore 146 of housing 116.

If modular head assembly 112 includes a polyaxial housing 116*a*, the spherically shaped head 124 of bone screw 114 will be permitted to freely rotate about the concave distal surface 170 of anvil 118 in multiple directions relative to the bone screw. In contrast, if modular head assembly 112 includes a uniplanar housing 116*b* or a transverse uniplanar housing 116*c*, the interaction between the protrusions 174*b*, 174*c* of the uniplanar housing or the transverse uniplanar housing, respectively, will restrict movement of the modular head assembly to a single axis relative to the bone screw 114. More particularly, uniplanar housing 116*b* will restrict movement of the modular head assembly to a front-back direction while transverse uniplanar housing 116*c* will restrict movement of the modular head assembly to a lateral-lateral direction (e.g., orthogonal to the front-back direction).

A spinal rod (not shown) may then be interconnected between adjacent modular head assemblies by inserting the spinal rod within the U-shaped openings 152 of each housing 116 and within the concave relief of the proximal surface 168 of anvil 118. Using a driving tool, the surgeon may then thread a set screw (not shown) to threads 142 of housing 116. As the set screw is threaded into housing 116 in the distal direction, the set screw exerts a distal directed force on anvil 118 and urges the ledges 165 from detents 147. Further threading of the set screw causes the spinal rod, anvil 118 and bone screw 114 to slide from a proximal portion 160 of the counterbore 146 into a distal portion 162 of the counterbore. The smaller diameter of distal portions 162 imparts an inwardly directed force on flanges 178 and causes the flanges to flex inwardly such that the lips 180 of the flanges clamp around the head 124 of bone screw 114, thereby fixing the rotational and angular position of the bone screw relative to housing 116 and preventing the bone screw from passing through a distal end of the housing.

Figure 16:
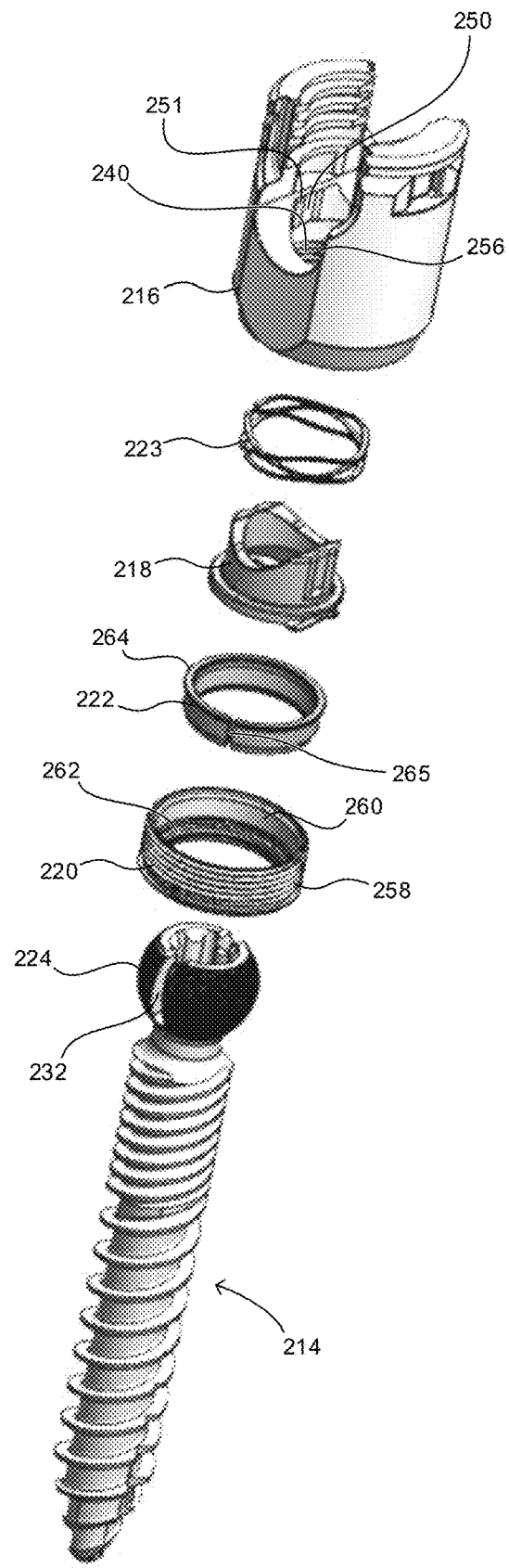
FIG. 16 is an exploded view of a modular pedicle screw assembly according to yet another embodiment of the present disclosure.

FIG. 16 illustrates a modular pedicle screw assembly 200 in accordance with yet another embodiment of the present disclosure. Modular pedicle screw assembly 200 is similar to modular pedicle screw assembly 10 but for the differences described hereinafter. When like features are referenced in connection with modular pedicle screw assembly 200, the previously described features are renumbered with sequential two hundred series numerals.

Pedicle screw assembly 200 includes a bottom loading modular head assembly 212 and a bone screw 214. Modular head assembly 212 includes a housing 216, an anvil 218, a cap 220, a retaining ring 222 and a biasing member 223. Housing 216 is formed generally similar to housing 16 but instead of defining longitudinal slots 50, a pair of guide posts 250 are formed on an inner surface of the wall defining the throughhole 240 of housing 216 in juxtaposed relation to one another. Each guide post 250 terminates at a stop 251 and is sized to cooperate with a correspondingly shaped recess on anvil 218 to enable the anvil to slidably translate along the guide post and to inhibit rotation of the anvil 218 within throughhole 240.

Assembly cap 220 includes an external threading 258 configured to threadably engage the threading 256 of housing 216 to assemble modular head assembly 212. Of course, other connection mechanisms such as a press fit connection may be used. Like assembly cap 20, an interior surface of assembly cap 220 defines a cavity for receiving retaining ring 222. The cavity of assembly cap 220 defines a first portion 260 (proximal portion) having a first diameter and a second portion 262 (distal portion) having a second diameter smaller than the first portion to allow retaining ring 222 to expand as the retaining ring translates proximally from the second portion of assembly cap to the first portion of the assembly cap. In contrast, as retaining ring 222 translates distally from the first portion 260 of assembly cap 220 to the second portion 262 of the assembly cap, the cavity is sized to compress retaining ring 222.

Retaining ring 222 has a substantially ring shaped body sized to be slidably received within the cavity of assembly cap 220 and a shelf 264 extending radially outward from a proximal end of the body. Shelf 264 has a relatively flat upper surface for engaging anvil 218 as retaining ring 222 translates within the cavity of assembly cap 220. Retaining ring 222 is formed of an elastic material, such as an elastic metal, or plastic, and defines a slit 265 extending therethrough from an outer surface of the ring-shaped body to the inner surface of the body. In this manner, retaining ring 222 is configured to compress upon the application of an external force (e.g., a compressive force applied to an outer surface of the body) and to expand upon the application of an internal force (e.g., an expansion force applied to an inner surface of the cylindrical body). In this regard, retaining ring 222 is designed to transition between a neutral (or unexpanded configuration), an expanded configuration in which the retaining ring is sized to receive the head 224 of bone screw 214 and a compressed configuration in which the retaining ring prevents the head of the bone screw from passing distally through the retaining ring.

Anvil 218 is formed similarly to anvil 18 and may be a polyaxial anvil, a uniplanar anvil, or a transverse uniplanar anvil (as such structures are detailed above). Put differently, anvil 218 may be a polyaxial anvil and have a smooth, concave, distal surface that, when used in conjunction with modular head assembly 212, will allow the modular head assembly to freely rotate (e.g., move in multiple axis) relative to bone screw 214. On the other hand, anvil 218 may be uniplanar anvil or a transverse uniplanar anvil that includes protrusions similar to protrusions 74b of uniplanar anvil 18b or protrusion 74c of transverse uniplanar anvil 18c that cooperate with groove 232 to restrict movement of modular head assembly 212 to a single axis relative to bone screw 14 and, more specifically, an axis in a front-back direction and an axis in a lateral-lateral direction, respectively.

Figure 17:
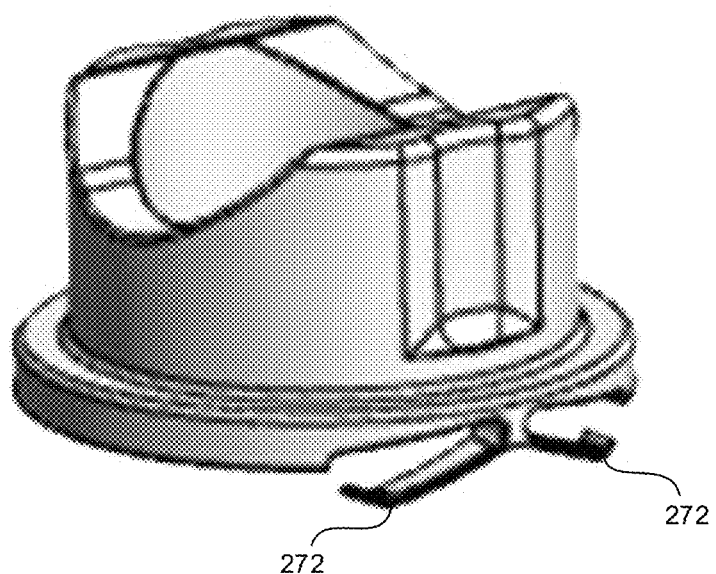
FIG. 17 is a perspective view of anvil for use in the modular pedicle screw assembly of FIG. 16.

With reference to FIG. 17, unlike anvil 18, anvil 218 does not include leaf springs that circumscribe the outer surface of the anvil. Instead, anvil 218, as shown, include leaf springs 272 that extend from a distal end of the anvil. In this regard, leaf springs 272 are positioned to engage the shelf 264 of retaining ring 222. As a result, when the head 224 of bone screw 214 is bottom loaded through retaining ring 222 and into engagement with the distal surface of the anvil, leaf springs 272 impart a biasing force on the retaining ring 222 to bias the retaining ring toward the distal portion 262 of cap 220 and prevent the head 224 of bone screw 212 from accidentally passing through the retaining ring as the modular head assembly is being manipulated.

Biasing member 223 is a low profiled spring, such as a wave spring, configured to sit around anvil 218 and to entirely circumscribe the outer surface of the anvil. When modular head assembly 212 is assembled, the wave spring is positioned to engage the annular face of the counterbore of the housing. As a result, when the head 224 of bone screw 214 is bottom loaded through retaining ring 222 and into engagement with anvil 218, the wave spring will impart a biasing force to the bone screw. This biasing force ensures that the distal surface of anvil 18 applies a constant distally directed force against the head of the bone screw and prevents modular head assembly 212 from "flopping" loosely about the head of the bone screw. In this manner, the biasing force affords the clinician greater control while securing modular head assembly 212 to bone screw 224. Furthermore, because the wave spring can be seated about anvil 218 prior to inserting the anvil into housing 216, modular head assembly 212 can be quickly and, more accurately, assembled without requiring a user to align and load individual springs within a pocket of the housing and/or pocket of the anvil prior to inserting the anvil into the housing in separate and consecutive steps.

Modular pedicle screw assembly 200 is assembled and used largely as described above with respect to modular pedicle screw assembly 10. For brevity, only the differences are described hereinafter. First, the surgeon (or other user such as a manufacturer), seats biasing member 223 around anvil 218 and slides the anvil into housing 216. Specifically, the recesses of anvil 218 are aligned about the guide posts 250 of housing 216 and the anvil is slid in a proximal direction. Retaining ring 222 may then be inserted into the 220 and before the cap is threaded to housing 216, thereby securing the anvil, the retaining ring, and the biasing member within the housing.

Next, with bone screw 214 secured at a desired location (e.g., implanted in a pedicle of a patient), modular head assembly 212 may be placed adjacent the head 224 of the bone screw and advanced in a distal direction over the head of the screw. As the head 224 of bone screw 214 is advanced proximally within throughhole 240, the head of the bone screw contacts retaining ring 222 and forces the retaining ring and anvil 218 in a proximal direction which, in turn, compresses biasing member 223 between the annular face of the counterbore and a flange of anvil 218. Distal movement of modular head assembly 212 relative to bone screw 214 will cause the head 224 of the bone screw to apply an outwardly directed force on retaining ring 222 and result in the resilient retaining ring transitioning from the neutral (or unexpanded) configuration to the expanded configuration. Retaining ring 222 is permitted to expand to the expanded configuration, in part, because the retaining ring is disposed within the larger proximal portion 260 of assembly cap 220.

Further movement of the modular head assembly 212 in the distal direction relative to bone screw 214, causes the head 224 of the bone screw to pass completely through the lumen of the retaining ring and into the contact with the distal surface of anvil 218. Again, due to biasing member 223, the distal surface of anvil 18 applies a constant distally directed force against the head 224 of bone screw 214 and prevents modular head assembly 212 from "flopping" loosely about the head of the bone screw.

Once the head 224 of bone screw 214 has passed completely through retaining ring 222, the retaining ring will elastically return to its neutral or unexpanded size. Leaf springs 272 will then immediately force retaining ring 222 toward the distal portion 262 of housing 216 and cause the retaining ring to transition from the neutral (unexpanded) configuration to a slightly compressed configuration, thereby preventing the head 224 of bone screw 214 from passing distally through the retaining ring as the surgeon manipulates housing 216. Put differently, if leaf spring 272 did not bias retaining ring 222 toward the distal portion 262 of retaining cap 220, certain manipulation techniques may cause the retaining ring to move proximally within the cap (via contact with the bone screw) thereby transitioning the retaining ring back to the neutral configuration and making the head 224 of bone screw 214 susceptible to incidentally passing distally through the retaining ring.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A pedicle screw assembly, comprising:
    a bone screw having a head and a shank, the head defining at least one groove; and
    a modular head assembly comprising:
        a housing having a proximal end and a distal end, the housing defining a throughbore extending along a longitudinal axis of the housing and between the proximal and distal ends of the housing;
        an anvil disposed within the throughbore such that the anvil is translatable along the axis and inhibited from rotating relative to the longitudinal axis; and
        a spring at least partially circumscribing an outer surface of the anvil and entirely disposed within the throughbore.

2. The assembly of claim 1, wherein the anvil includes a contact surface for engaging the head of the bone screw and the contact surface includes at least one protrusion sized and shaped to be received by the at least one groove for restricting movement of the bone screw to a single plane.

3. The assembly of claim 2, wherein the at least one groove includes two grooves diametrically opposed from one another about the head of the bone screw, and wherein the at least one protrusion comprises two protrusions diametrically opposed from one another about the contact surface of the anvil.

4. The assembly of claim 2, wherein the anvil comprises a plurality of flanges and the plurality of flanges collectively form a cavity for receiving the head of the bone screw.

5. The assembly of claim 4, wherein each one of the plurality of flanges is moveable between an outwardly flexed configuration in which the cavity is sized to receive the head of the bone screw and an inwardly flexed configuration in which the flanges clamp the head of the bone screw.

6. The assembly of claim 5, wherein each one of the plurality of flanges includes a lip at a distal end of the flange, and wherein the throughbore of the housing forms an anvil receiving cavity having a proximal portion with a first diameter and a distal portion with a second diameter smaller than the first diameter, and movement of the lips from the proximal portion of the anvil receiving cavity to the distal portion of the anvil receiving cavity transitions the flanges from the outwardly flexed configuration to the inwardly flexed configuration.

7. The assembly of claim 6, wherein the anvil cavity defines a detent and an outer surface of the anvil comprises a laterally extending ledge sized to be received by the detent for retaining the anvil in a position in which the lips of the flanges are positioned within the proximal portion of the anvil receiving cavity.

8. The assembly of claim 4, wherein adjacent ones of the plurality of flanges are spaced to define a gap and the at least one protrusion extends through the gap and into the at least one groove of the head of the bone screw.

9. The assembly of claim 1, wherein an annular face of the throughbore defines a longitudinal slot extending substantially parallel to the longitudinal axis of the housing.

10. The assembly of claim 9, wherein the anvil comprises a lug provided on an outer surface of the anvil, the lug being slidably received within the longitudinal slot to prevent rotation of the anvil with respect to the housing.

11. The assembly of claim 1, wherein the spring is a leaf spring at least partially circumscribing an outer surface of the anvil.

12. The assembly of claim 1, wherein the anvil comprises a leaf spring extending from a distal end thereof.

13. The assembly of claim 12, wherein the spring is a wave spring arranged about an outer surface of the anvil.

14. The assembly of claim 1, wherein the distal end of the housing comprises a thread, and wherein the modular head assembly further comprises a cap having a corresponding thread configured to engage the thread of the housing to secure the cap to the housing.

15. The assembly of claim 1, wherein the modular head assembly further comprises:
a cap coupled to the housing, the cap forming a retaining ring receiving portion having a proximal portion defining a first diameter and a distal portion defining a second diameter smaller than the first diameter; and
a retaining ring formed of a resilient material disposed within the retaining ring receiving portion, the retaining ring being transitionable between an expanded configuration in which the retaining ring is sized to receive the head of the bone screw and a compressed configuration in which the retaining ring prevents the head of the bone screw from passing distally through the retaining ring.

16. The assembly of claim 15, wherein movement of the retaining ring from the proximal portion of the retaining ring receiving portion to the distal portion of the retaining ring receiving portion transitions the retaining ring from the expanded configuration to the compressed configuration.

17. A spinal fixation kit, comprising:
a bone screw having a head and a shank, the head defining at least one arcuate groove extending about the head of the bone screw in a longitudinal direction;
a first modular head assembly comprising:
a first housing having a first proximal end and a first distal end, and defining a first throughbore extending between the first proximal end and the first distal end of the first housing; and
a first anvil disposed within the first throughbore, wherein the first housing is configured to receive the head of the bone screw and allow the first housing to move about multiple axes relative to the bone screw; and
a second modular head assembly comprising:
a second housing having a second proximal end and a second distal end, and defining a second throughbore extending between the second proximal end and the second distal end of the housing; and
a second anvil disposed within the second throughbore, the second anvil including a protrusion sized to be received by the at least one groove of the bone screw to restrict relative movement between the second housing and the bone screw to a single plane.

18. The kit of claim 17, further comprising:
a spinal rod; and
a set screw for securing the spinal rod to one of the first or second housing.

19. A spinal fixation kit, comprising:
a bone screw having a head and a shank, the head defining a pair of arcuate grooves extending about the head of the bone screw in a longitudinal direction;
a first modular head assembly comprising:
a first housing having a first proximal end and a first distal end, and defining a first throughbore extending between the first proximal end and the first distal end of the first housing; and
a first anvil disposed within the first throughbore, wherein the first housing is configured to receive the bone screw and allow the first housing to move about multiple axes relative to the bone screw; and
a second modular head assembly comprising:
a second housing having a second proximal end and a second distal end, and defining a second throughbore extending between the second proximal end and the second distal end of the second housing; and
a second anvil disposed within the second throughbore, wherein the second modular head assembly includes a pair of protrusions, each one of the protrusions being sized to be received by a respective one of the pair of grooves to restrict relative movement between the second housing and the bone screw to a single plane, the single plane intersecting the pair of protrusions.

20. The kit of claim 19, wherein at least one of the first anvil and the second anvil comprises a plurality of flanges collectively forming a cavity for receiving the head of the bone screw, and wherein adjacent flanges are spaced a distance apart from one another to form a gap through which a respective one of the protrusions extends.

* * * * *